(12) United States Patent
Prammer et al.

(10) Patent No.: US 7,733,086 B2
(45) Date of Patent: Jun. 8, 2010

(54) SYSTEMS AND METHODS FOR DEEP-LOOKING NMR LOGGING

(75) Inventors: Manfred G. Prammer, Downingtown, PA (US); Sergey Knizhnik, Exton, PA (US); Stefan K. Menger, Exton, PA (US); George D. Goodman, Phoenixville, PA (US); Edward J. Harris, III, Sanatoga, PA (US); Earle Drack, Spring City, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 37 days.

(21) Appl. No.: 12/261,343

(22) Filed: Oct. 30, 2008

(65) Prior Publication Data
US 2009/0072825 A1 Mar. 19, 2009

Related U.S. Application Data

(62) Division of application No. 10/837,084, filed on Apr. 30, 2004, now Pat. No. 7,463,027.

(60) Provisional application No. 60/467,568, filed on May 2, 2003, provisional application No. 60/508,778, filed on Oct. 4, 2003.

(51) Int. Cl.
*G01V 3/00* (2006.01)
(52) U.S. Cl. ...................... 324/303; 324/300
(58) Field of Classification Search ......... 324/300–322; 323/324–343; 702/6
See application file for complete search history.

(56) References Cited
U.S. PATENT DOCUMENTS 1,158,959 A 11/1915 Beach
2,262,655 A 11/1941 Seale
2,705,790 A 4/1955 Hahn
2,912,641 A 11/1959 Ruble
2,973,471 A 2/1961 Armistead et al.
3,011,554 A 12/1961 Desbrandes et al.
3,205,477 A 9/1965 Kalbfell
3,209,588 A 10/1965 Terry (Continued)

FOREIGN PATENT DOCUMENTS

EP 0 295 134 A2 12/1988

(Continued)

OTHER PUBLICATIONS

Abragam, The Principles of Nuclear Magnetism, 1961 (whole book).

(Continued)

*Primary Examiner*—Brij B Shrivastav
(74) *Attorney, Agent, or Firm*—Jones Day

(57) ABSTRACT

An NMR logging tool for conducting NMR measurements in a plurality of sensitive volumes ranging up to a meter from the tool. The tool comprises a magnetic assembly using one or more permanent magnets and at least one pole piece for extending a magnet pole and shaping the magnetic field to simulate a magnetic monopole in a sensitive volume within the formation. Different embodiments of a segmented antenna enable directional NMR logging. The tool embodiments and methods of their use are suitable for wireline or LWD logging, and can be used for directional drilling.

26 Claims, 25 Drawing Sheets

U.S. PATENT DOCUMENTS

| | | |
|---|---|---|
| 3,212,574 A | 10/1965 | Fox |
| 3,213,357 A | 10/1965 | Brown et al. |
| 3,360,716 A | 12/1967 | Bloom et al. |
| 3,395,337 A | 7/1968 | Varian |
| 3,402,344 A | 9/1968 | Brown et al. |
| 3,427,532 A | 2/1969 | Nelson |
| 3,452,592 A | 7/1969 | Voetter |
| 3,453,433 A | 7/1969 | Alger et al. |
| 3,508,438 A | 4/1970 | Alger et al. |
| 3,528,000 A | 9/1970 | Schwede |
| 3,567,935 A | 3/1971 | Nagel |
| 3,567,936 A | 3/1971 | Tittman |
| 3,577,782 A | 5/1971 | Aitken |
| 3,590,228 A | 6/1971 | Burke |
| 3,593,116 A | 7/1971 | Culpepper |
| 3,617,867 A | 11/1971 | Herzog |
| 3,638,484 A | 2/1972 | Tixier |
| 3,657,730 A | 4/1972 | Robinson et al. |
| 3,667,035 A | 5/1972 | Slichter |
| 3,777,560 A | 12/1973 | Guignard |
| 3,784,898 A | 1/1974 | Darley et al. |
| 3,896,668 A | 7/1975 | Anderson et al. |
| 4,210,018 A | 7/1980 | Brieger |
| 4,291,271 A | 9/1981 | Lauffer |
| 4,292,842 A | 10/1981 | Hallmark |
| 4,310,887 A | 1/1982 | Suau |
| 4,339,948 A | 7/1982 | Hallmark |
| 4,350,955 A | 9/1982 | Jackson et al. |
| 4,424,487 A | 1/1984 | Lauffer |
| 4,470,456 A | 9/1984 | Moutray et al. |
| 4,479,564 A | 10/1984 | Tanguy |
| 4,528,508 A | 7/1985 | Vail, III |
| 4,536,711 A | 8/1985 | King et al. |
| 4,536,714 A | 8/1985 | Clark |
| 4,625,547 A | 12/1986 | Lyle, Jr. |
| 4,629,986 A | 12/1986 | Clow et al. |
| 4,629,987 A | 12/1986 | King et al. |
| 4,638,251 A | 1/1987 | King |
| 4,656,422 A | 4/1987 | Vail, III et al. |
| 4,686,364 A | 8/1987 | Herron |
| 4,700,142 A | 10/1987 | Kuckess |
| 4,707,658 A | 11/1987 | Frahm et al. |
| 4,710,713 A | 12/1987 | Strikman |
| 4,714,881 A | 12/1987 | Givens |
| 4,717,876 A | 1/1988 | Masi et al. |
| 4,717,877 A | 1/1988 | Taicher et al. |
| 4,717,878 A | 1/1988 | Taicher et al. |
| 4,728,892 A | 3/1988 | Vinegar et al. |
| 4,742,459 A | 5/1988 | Lasseter et al. |
| 4,761,889 A | 8/1988 | Cobern et al. |
| 4,769,602 A | 9/1988 | Vinegar et al. |
| 4,777,464 A | 10/1988 | Takabatashi et al. |
| 4,783,742 A | 11/1988 | Peter |
| 4,785,245 A | 11/1988 | Lew et al. |
| 4,792,757 A | 12/1988 | Vail, III et al. |
| RE32,913 E | 4/1989 | Clark |
| 4,825,163 A | 4/1989 | Yabusaki et al. |
| 4,829,252 A | 5/1989 | Kaufman |
| 4,860,581 A | 8/1989 | Zimmerman et al. |
| 4,875,013 A | 10/1989 | Murakami et al. |
| 4,885,540 A | 12/1989 | Snoddy et al. |
| 4,890,487 A | 1/1990 | Dussan et al. |
| 4,899,112 A | 2/1990 | Clark et al. |
| 4,931,760 A | 6/1990 | Yamaguchi et al. |
| 4,933,638 A | 6/1990 | Kenyon et al. |
| 4,933,640 A | 6/1990 | Kuckes |
| 4,936,139 A | 6/1990 | Zimmerman et al. |
| 4,939,648 A | 7/1990 | O'Neill et al. |
| 4,949,045 A | 8/1990 | Clark et al. |
| 4,951,749 A | 8/1990 | Carroll |
| 4,956,921 A | 9/1990 | Coles |
| 4,958,125 A | 9/1990 | Jardine et al. |
| 4,987,368 A | 1/1991 | Vinegar |
| 4,994,777 A | 2/1991 | Leupold et al. |
| 5,023,551 A | 6/1991 | Kleinberg et al. |
| 5,055,787 A | 10/1991 | Kleinberg et al. |
| 5,055,788 A | 10/1991 | Kleinberg et al. |
| 5,056,595 A | 10/1991 | Desbrandes |
| 5,122,746 A | 6/1992 | King et al. |
| 5,138,263 A | 8/1992 | Towle |
| 5,200,699 A | 4/1993 | Baldwin et al. |
| 5,212,447 A | 5/1993 | Paltiel |
| 5,233,866 A | 8/1993 | Desbrandes |
| 5,235,285 A | 8/1993 | Clark et al. |
| 5,265,015 A | 11/1993 | Auzerais et al. |
| 5,269,180 A | 12/1993 | Dave et al. |
| 5,279,153 A | 1/1994 | Dussan et al. |
| 5,280,243 A | 1/1994 | Miller et al. |
| 5,291,137 A | 3/1994 | Freedman |
| 5,293,931 A | 3/1994 | Nichols et al. |
| 5,299,128 A | 3/1994 | Antoine et al. |
| 5,309,098 A | 5/1994 | Coates et al. |
| 5,329,448 A | 7/1994 | Rosthal |
| 5,329,811 A | 7/1994 | Schultz et al. |
| 5,337,822 A | 8/1994 | Massie et al. |
| 5,349,184 A | 9/1994 | Wraight |
| 5,350,925 A | 9/1994 | Watson |
| 5,359,324 A | 10/1994 | Clark et al. |
| 5,363,041 A | 11/1994 | Sezginer |
| 5,365,171 A | 11/1994 | Buess et al. |
| 5,376,884 A | 12/1994 | Sezginer |
| 5,379,216 A | 1/1995 | Head |
| 5,381,092 A | 1/1995 | Freedman |
| 5,387,865 A | 2/1995 | Jerosch-Herold et al. |
| 5,389,877 A | 2/1995 | Sezginer et al. |
| 5,397,989 A | 3/1995 | Spraul et al. |
| 5,400,786 A | 3/1995 | Allis |
| 5,412,320 A | 5/1995 | Coates |
| 5,417,104 A | 5/1995 | Wong |
| 5,432,446 A | 7/1995 | Macinnis et al. |
| 5,453,692 A | 9/1995 | Takahashi et al. |
| 5,486,761 A | 1/1996 | Sezginer |
| 5,486,762 A | 1/1996 | Freedman et al. |
| 5,497,087 A | 3/1996 | Vinegar et al. |
| 5,498,960 A | 3/1996 | Vinegar et al. |
| 5,517,115 A | 5/1996 | Prammer |
| 5,536,938 A | 7/1996 | Miller et al. |
| 5,557,200 A | 9/1996 | Coates |
| 5,557,201 A | 9/1996 | Kleinberg et al. |
| 5,557,205 A | 9/1996 | Ohta et al. |
| 5,565,775 A | 10/1996 | Stallmach et al. |
| 5,574,417 A | 11/1996 | Dorri et al. |
| 5,596,274 A | 1/1997 | Sezginer |
| 5,602,334 A | 2/1997 | Proett et al. |
| 5,629,623 A | 5/1997 | Sezginer et al. |
| 5,644,076 A | 7/1997 | Proett et al. |
| 5,644,231 A | 7/1997 | Wignall et al. |
| 5,652,517 A | 7/1997 | Maki et al. |
| 5,672,819 A | 9/1997 | Chin et al. |
| 5,675,147 A | 10/1997 | Ekstrom et al. |
| 5,680,043 A | 10/1997 | Hurlimann et al. |
| 5,696,448 A | 12/1997 | Coates et al. |
| 5,701,112 A | 12/1997 | Brown |
| 5,705,927 A | 1/1998 | Sezginer et al. |
| 5,712,566 A | 1/1998 | Taicher et al. |
| 5,741,962 A | 4/1998 | Birchak et al. |
| 5,757,186 A | 5/1998 | Taicher et al. |
| 5,757,191 A | 5/1998 | Gianzero |
| 5,767,674 A | 6/1998 | Griffin et al. |
| 5,796,252 A | 8/1998 | Kleinberg et al. |
| 5,826,662 A | 10/1998 | Beck et al. |
| 5,828,214 A | 10/1998 | Taicher et al. |
| 5,834,936 A | 11/1998 | Taicher et al. |
| 5,869,755 A | 2/1999 | Ramamoorthy et al. |

| | | |
|---|---|---|
| 5,914,598 A | 6/1999 | Sezginer et al. |
| 5,923,167 A | 7/1999 | Chang et al. |
| 5,934,374 A | 8/1999 | Hrametz et al. |
| 5,936,405 A | 8/1999 | Prammer et al. |
| 5,959,453 A | 9/1999 | Taicher et al. |
| 5,977,768 A | 11/1999 | Sezginer et al. |
| 5,992,519 A | 11/1999 | Ramakrishnan et al. |
| 6,005,389 A | 12/1999 | Prammer |
| 6,008,646 A | 12/1999 | Griffin et al. |
| 6,018,243 A | 1/2000 | Taicher et al. |
| 6,023,163 A | 2/2000 | Flaum et al. |
| 6,023,164 A | 2/2000 | Prammer |
| 6,046,587 A | 4/2000 | King et al. |
| 6,049,205 A | 4/2000 | Taicher et al. |
| 6,051,973 A | 4/2000 | Prammer |
| 6,065,335 A | 5/2000 | Denz et al. |
| 6,065,355 A | 5/2000 | Schultz |
| 6,069,479 A | 5/2000 | Taicher et al. |
| 6,081,116 A | 6/2000 | Wu et al. |
| 6,107,796 A | 8/2000 | Prammer |
| 6,107,797 A | 8/2000 | Sezginer |
| 6,111,408 A | 8/2000 | Blades et al. |
| 6,111,409 A | 8/2000 | Edwards et al. |
| 6,114,851 A | 9/2000 | Kruspe et al. |
| 6,115,671 A | 9/2000 | Fordham et al. |
| 6,118,272 A | 9/2000 | Taicher et al. |
| 6,121,773 A | 9/2000 | Taicher et al. |
| 6,121,774 A | 9/2000 | Sun |
| 6,133,734 A | 10/2000 | McKeon |
| 6,133,735 A | 10/2000 | Hurlimann et al. |
| 6,140,817 A | 10/2000 | Flaum et al. |
| 6,163,154 A | 12/2000 | Anderson et al. |
| 6,166,543 A | 12/2000 | Sezginer et al. |
| 6,173,793 B1 | 1/2001 | Thompson et al. |
| 6,176,323 B1 | 1/2001 | Weirich et al. |
| 6,204,663 B1 | 3/2001 | Prammer |
| 6,216,782 B1 | 4/2001 | Skinner |
| 6,218,833 B1 | 4/2001 | Kruspe et al. |
| 6,229,308 B1 | 5/2001 | Freedman |
| 6,232,778 B1 | 5/2001 | Speier et al. |
| 6,237,404 B1 | 5/2001 | Crary et al. |
| 6,242,912 B1 | 6/2001 | Prammer et al. |
| 6,242,913 B1 | 6/2001 | Prammer |
| 6,246,236 B1 | 6/2001 | Poitzsch et al. |
| 6,252,405 B1 | 6/2001 | Watkins et al. |
| 6,253,155 B1 | 6/2001 | Hagiwara |
| 6,255,817 B1 | 7/2001 | Poitzsch et al. |
| 6,255,818 B1 | 7/2001 | Heaton et al. |
| 6,255,819 B1 | 7/2001 | Day et al. |
| 6,268,726 B1 | 7/2001 | Prammer et al. |
| 6,274,865 B1 | 8/2001 | Schroer et al. |
| 6,297,632 B1 | 10/2001 | Speier |
| 6,301,959 B1 | 10/2001 | Hrametz et al. |
| 6,327,538 B1 | 12/2001 | Chin |
| 6,344,744 B2 | 2/2002 | Taicher et al. |
| 6,346,813 B1 | 2/2002 | Kleinberg |
| 6,362,619 B2 | 3/2002 | Prammer et al. |
| 6,392,409 B1 | 5/2002 | Chen |
| 6,492,809 B1 | 12/2002 | Speier et al. |
| 6,512,371 B2 | 1/2003 | Prammer |
| 6,518,754 B1 | 2/2003 | Edwards |
| 6,518,756 B1 | 2/2003 | Morys et al. |
| 6,518,758 B1 | 2/2003 | Speier et al. |
| 6,525,534 B2 | 2/2003 | Akkurt et al. |
| 6,531,868 B2 | 3/2003 | Prammer |
| 6,541,969 B2 | 4/2003 | Sigal et al. |
| 6,559,640 B2 | 5/2003 | Taicher |
| 6,563,314 B1 | 5/2003 | Kleinberg |
| 6,577,125 B2 | 6/2003 | Prammer et al. |
| 6,583,621 B2 | 6/2003 | Prammer et al. |
| 6,586,931 B2 | 7/2003 | Taicher |
| 6,646,437 B1 | 11/2003 | Chitale et al. |
| 6,661,226 B1 | 12/2003 | Hou et al. |
| 6,688,390 B2 | 2/2004 | Bolze et al. |
| 6,717,404 B2 | 4/2004 | Prammer |
| 6,729,399 B2 | 5/2004 | Follini et al. |
| 6,737,864 B2 | 5/2004 | Prammer et al. |
| 6,748,328 B2 | 6/2004 | Storm, Jr. et al. |
| 6,766,854 B2 | 7/2004 | Ciglenec et al. |
| 6,825,657 B2 | 11/2004 | Kleinberg et al. |
| 6,833,699 B2 | 12/2004 | Galford et al. |
| 6,838,875 B2 | 1/2005 | Freedman |
| 6,859,032 B2 | 2/2005 | Heaton et al. |
| 6,891,369 B2 | 5/2005 | Hurlimann et al. |
| 6,987,385 B2 | 1/2006 | Akkurt et al. |
| 7,463,027 B2 * | 12/2008 | Prammer et al. ............ 324/303 |
| 2002/0163334 A1 | 11/2002 | Hagiwara |
| 2003/0066646 A1 | 4/2003 | Shammai et al. |
| 2003/0094040 A1 | 5/2003 | Proett et al. |
| 2004/0055400 A1 | 3/2004 | Ringgenberg et al. |
| 2005/0030021 A1 | 2/2005 | Prammer et al. |

FOREIGN PATENT DOCUMENTS

| | | |
|---|---|---|
| EP | 0489578 | 12/1991 |
| EP | 0 581 666 A3 | 2/1994 |
| EP | 0 649 035 B1 | 4/1995 |
| EP | 0 689 722 | 1/1996 |
| GB | 2 056 082 A | 7/1980 |
| GB | 2 310 500 | 8/1997 |
| GB | 2 341 448 A | 3/2000 |
| GB | 2 341 685 A | 3/2000 |
| GB | 2348222 | 9/2000 |
| GB | 2 396 648 A | 6/2004 |
| JP | 404332107 A | 11/1992 |
| JP | 404346089 A | 12/1992 |
| WO | WO 92/10768 | 6/1992 |
| WO | WO 96/12976 | 5/1996 |
| WO | WO 97/14063 | 4/1997 |
| WO | WO 98/25164 | 6/1998 |
| WO | WO 98/29639 | 7/1998 |
| WO | WO 00/14576 | 3/2000 |
| WO | WO 01/42807 | 6/2001 |

OTHER PUBLICATIONS

Akkurt et al., "NMR Logging of Natural Gas Reservoirs," SPWLA 36th Annual Logging Symposium (Jun. 26-29, 1995).

Akkurt et al., "Selection of Optimal Acquisition Parameters for MRIL Logs," SPWLA 37th Annual Logging Symposium, Jun. 16-19, 1996.

Appel et al., "Reservoir fluid study by nuclear magnetic resonance," Paper: SPWLA, presented at the $41^{st}$ Annual Logging Symposium, Jun. 4-27, 2000, Dallas, TX.

Ayan et al., "Measuring Permeability Anisotropy: The Latest Approach", Oilfield Review vol. 6, No. 4, pp. 24-35, Oct. 1994.

Bloembergen et al., "Relaxation effects in nuclear magnetic resonance absorption," Phys Rev, Apr. 1, 1948;73(7):679-712.

Brown et al., "Nuclear Magnetism Logging," Transactions of the American Institute of Mining, Metallurgical, and Petroleum Engineers, vol. 219 (1960), pp. 199-207.

Brown, "Proton relaxation in crude oils," Nature, Feb. 4, 1961;189(4762):387-9.

Brownstein et al., "Importance of classical diffusion in NMR studies of water in biological cells," The American Physical Society, vol. 19, No. 6, (1979) pp. 2446-2453.

Burley et al., IUN/FYDE Introductory Physics Notes, http://theory.uwinnipeg.ca/physics/index.htm, Feb. 5, 1996; specifically .../physics/curr/node3.html, .../node6.html, and .../node7.html.

Cannon et al., "Quantitative NMR Interpretation," Society of Petroleum Engineers, SPE 49010, 1998.

Carr et al., "Effects of Diffusion on Free Precision in Nuclear Magnetic Resonance Experiments," *Physical Review*, vol. 94. No. 3 (May 1, 1954), pp. 630-638.

Chandler et al., "Improved Log Quality with a Dual-Frequency Pulsed NMR Tool," *Society of Petroleum Engineers* (1994) pp. 23-35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Estimation of Hydrocarbon Viscosity with Multiple TE Dual Wait-Time MRIL Logs," Society of Petroleum Engineers, SPE 49009, 1998.

Chen et al., "Improving the Accuracy of NMR Relaxation Distribution Analysis in Clay-Rich Reservoirs and Core Samples," paper SCA 9702, in 1997 international symposium proceedings: Society of Professional Well Log Analysts, Society of Core Analysts Chapter-at-large, p. 10, 1997.

Clavier et al., "Theoretical and Experimental Bases for the Dual-Water Model for Interpretation of Shaly Sands," Society of Petroleum Engineers Journal, 1984, pp. 153-168.

Close et al., "Measurement of BHA Vibration Using MWD," IADC/SPE Drilling Conference, Feb. 28, 1988-Mar. 2, 1988.

Coates et al., "A New Approach to Improved Log-Derived Permeability," SPWLA Fourteenth Annual Logging Symposium, May 6-9, 1973, pp. 1-27.

Coates et al., "An Investigation of a New Magnetic Resonance Imaging Log," National SPWLA Convention (Jun. 18, 1991), pp. 1-24.

Coates et al., "Applying NMR Total and Effective Porosity to Formation Evaluation," Society of Petroleum Engineers, Inc., SPE 38736, 1997.

Coates et al., "Core Data and the MRIL Show—A New Approach to 'Formation Factor,'" National SPWLA Convention (Jun. 15, 1992), pp. 1-15.

Coates et al., "The Magnetic Resonance Imaging Log Characterized by Comparison With Petrophysical Properties and Laboratory Core Data," Society of Petroleum Engineers, SPE 22723, 1991, pp. 627-635.

Davidson et al., Soil Mechanics, http://fbe.uwe.ac.uk/public/geocal/SoilMech/water/water.htm, May 2000.

Delhomme et al., "Permeability and Porosity Upscaling in the Near-Wellbore Domain: The Contribution of Borehole Electrical Images", SPE 36822, Europ. Petrol. Conf. Oct. 22-24, 1996,89-101.

Dunn et al., "A Method for Inverting NMR Data Sets With Different Signal to Noise Ratios," SPWLA 39th Annual Logging Symposium, May 26-29, 1998.

Edwards et al., "Improved NMR Well Logs From Time-Dependent Echo Filtering," SPWLA 37th Annual Logging Symposium, Jun. 16-19, 1996.

Edwards, Carl M., "Effects of Tool Design and Logging Speed on T2 NMR Log Data," SPWLA 38th Annual Logging Symposium, Jun. 15-18, 1997.

Ezzedine et al., "Bayesian Integration of Hydrogeological and Geophysical Data for Site Characterization: Theory and Application to the LLNL Superfund Site", Berkely CA, Mar. 25-28, 2002.

Farrar et al., "Pulse and Fourier Transform NMR Introduction to Theory and Methods," Academic Press (1971) pp. 26-29.

Freedman et al., "Combining NMR and Density Logs for Petrophysical Analysis in Gas-Bearing Formations," SPWLA 39th Annual Logging Symposium, May 26-29, 1998.

Freedman et al., A new NMR method of fluid characterization in reservoir rocks: Experimental confirmation and simulation results, SPE-63214:717-31, Society of Petroleum Engineers Inc., presented at the $75^{th}$ Annual Technical Conference and Exhibition, Oct. 1-4, 2000, Dallas TX.

Gallegos et al., "A NMR Technique for the Analysis of Pore Structure: Application to Materials with Well-Defined Pore Structure," Journal of Colloid and Interface Science, Vol. 119, No. 1, Sep. 1987, pp. 127-140.

Gallegos et al., "A NMR Technique for the Analysis of Pore Structure: Determination of Continuous Pore Size Distributions," Journal of Colloid and Interface Science, vol. 122, No. 1, Mar. 1988, pp. 143-153.

Georgi et al., "On the Relationship between Resistivity and Permeability Anisotropy", SPE 77715, 77th Ann. Techn. Conf. of the SPE, Sep. 29-Oct. 2, 2002 (14 pages).

Herrick et al., "An Improved Nuclear Magnetism Logging System and its Application to Formation Evaluation," Society of Petroleum Engineers, SPE 8361, 1979.

Hou et al., "Nuclear Magnetic Resonance Logging Methods for Fluid Typing," Society of Petroleum Engineers, Inc., SPE 48896, 1998.

Howard et al., "Proton Magnetic Resonance and Pore-Size Variations in Reservoir Sandstones," Society of Petroleum Engineers (1990), pp. 733-741.

Hull et al., "Field Examples of Nuclear Magnetism Logging," Journal of Petroleum Technology, 1960, pp. 14-22.

Jackson et al., "Western Gas Sands Project Los Alamos NMR Well Logging Tool Development," Los Alamos National Laboratory (Oct. 1981-Sep. 1982) pp. 1-28.

Jackson, Jasper A., "Nuclear Magnetic Resonance Well Logging," The Log Analyst, Sep.-Oct. 1984, pp. 16-30.

Jansen, "Whirl and Chaotic Motion of Stabilized Drill Collars," SEP 20930, Jun. 1992.

Joshi, Horizontal Well Technology, Pennwell Publishing Company, 1991.

Kenyon et al., "Nuclear Magnetic Resonance Imaging—Technology for the $21^{st}$ Century," Schlumberger Oilfield Review, Autumn 1995.

Kenyon et al., "Pore-Size Distribution and NMR in Microporous Cherty Sandstones," SPWLA Thirtieth Annual Logging Symposium (Jun. 11-14, 1989), pp. 1-24.

Kleinberg et al., "NMR Properties of Reservoir Fluids," The Log Analyst, Nov.-Dec. 1996, pp. 20-32.

Kleinberg et al., "Novel NMR Apparatus for Investigating an External Sample," Journal of Magnetic Resonance, (1992) pp. 466-485.

Kleinberg et al., "Nuclear Magnetic Resonance of Rocks: T1 vs. T2," Society of Petroleum Engineers, SPE 26470, 1993, pp. 553-563.

Lindsay et al., "Sequential Backus Averaging: Upscaling well logs to seismic wavelengths", The Leading Edge, vol. 20, Issue 2, pp. 188-191 (Feb. 2001).

Lo et al., "Relaxation time and diffusion measurements of methane and n-decane mixtures," The Log Analyst, Nov.-Dec. 1998;43-7.

Lo et al., Correlations of NMR relaxation time with viscosity, diffusivity, and gas/oil ratio of methane/hydrocarbon mixtures, SPE 63217:757-71, Society of Petroleum Engineers, presented at the $75^{th}$ Annual Technical Conference and Exhibition, Oct. 1-4, 2000, Dallas, TX.

McKeon et al., "An Improved NMR Tool Design for Faster Logging", SPWLA, $40^{th}$ Annual Logging Symposium, May-Jun. 1999.

Menger et al., "A New Algorithm for Analysis of NMR Logging Data," Society of Petroleum Engineers, Inc., SPE 49013, 1998.

Mesri et al., "Mechanisms controlling the permeability of clays," Clays and Clay Minerals, 1971, 19:151-158.

Miller et al., "Spin Echo Magnetic Resonance Logging: Porosity and Free Fluid Index Determination," Society of Petroleum Engineers, SPE 20561 (1990), pp. 321-334.

Morriss et al., "Field Test of an Experimental Pulsed Nuclear Magnetism Tool," SPWLA Annual Logging Symposium (Jun. 13-16, 1993), pp. 1-23.

Morriss et al., "Hydrocarbon Saturation and Viscosity Estimation from NMR Logging in the Belridge Diatomite," 35th SPWLA Annual Logging Symposium (Jun. 19-22, 1994), pp. 1-24.

Moulton et al., "Multilevel upscaling in heterogeneous porous media", Research Highlights LA-UR 99/4754, Center for Nonlinear Studies, Los Alamos National Laboratory, Jan. 1999.

Nascimento et al., "Anomalous NMR Responses in Highly Permeable Sandstone Reservoirs: A Case Study," SPWLA 40th Annual Logging Symposium, May 30-Jun. 3, 1999.

Nelson, "Permeability-porosity relationships in sedimentary rocks," The Log Analyst, May-Jun. 1994, 38-62.

Neuman et al., "Applications of Nuclear Magnetism Logging to Formation Evaluation," Journal of Petroleum Technology, vol. 34, (1982) pp. 2853-2862.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195-260.

Prammer et al., "A New Multiband Generation of NMR Logging Tools," Society of Petroleum Engineers, SPE 49011, 1998, Only year of publication is available.

Prammer et al., "Measurements of Clay-Bound Water and Total Porosity by Magnetic Resonance Logging," Society of Petroleum Engineers, SPE 36522, 1996, Only year of publication is available.

Prammer et al., "Theory and Operation of a New, Multi-Volume, NMR Logging System," SPWLA 40th Annual Logging Symposium, May 30-Jun. 3, 1999.

Prammer, et al., "Lithology-Independent Gas Detection by Gradient NMR Logging," Society of Petroleum Engineers, paper SPE-30562, published in the transactions to the 1995 SPE Annual Technical Conference & Exhibition, pp. 325-336, (1995).

Prammer, M.G., "NMR Pore Size Distributions and Permeability at the Well Site," *Society of Petroleum Engineers*, SPE 28368, (1994) pp. 55-64.

Proett et al., "New wireline formation testing tool with advanced sampling technology," SPE 56711:483-98, Society of Petroleum Engineers Inc., presented at the 74$^{th}$ Annual Technical Conference and Exhibition, Oct. 3-6, 1999, Houston, TX.

Revil et al., "Permeability of shaly sands," Water Resources Research, Mar. 1999, 35(3): 651-662.

*Schlumberger Wireline & Testing*, "Combinable Magnetic Resonance tool reliably indicates, water-free production and reveals hard-to-find pay zones," (Jun. 1995), Only year is available.

Setser et al., "Measurement of Remaining Oil Saturation in Northern Michigan Using Nuclear Magnetism Log Data and Pressure Core," Society of Petroleum Engineers, SPE 14276, 1985, Only year is available.

Singer et al., "Fast NMR Logging for Bound Fluid and Permeability," SPWLA 38th Annual Logging Symposium, Jun. 15-18, 1997.

Straley et al., "NMR in Partially Saturated Rocks: Laboratory Insights on Free Fluid Index and Comparison with Borehole Logs," SPWLA Annual Logging Symposium (Jun. 27, 1991) pp. 40-56.

Tabanou et al., "Thinly laminated reservoir evaluation in oil-base mud: High resolution versus bulk anisotropy measurement—a comprehensive evaluation," SPWLA 43$^{rd}$ Ann. Logging Symp. (14 pages).

Tang et al., "LP-ZOOM, a Linear Prediction Method for Local Spectral Analysis of NMR Signals," Journal of Magnetic Resonance 79, 190-196 (1988).

The Mathworks, Inc., Image Processing Toolbox for Use with MATLAB, User's Guide, Version 2, May 1997.

Van Baaren, "Quick-look permeability estimates using sidewall samples and porosity logs," 6th Ann. European Logging Symp. Transactions, SPWLA, 1979, Only year of publication is available.

Van Dussen et al., "Determination of hydrocarbon properties by optical analysis during wireline fluid sampling," SPE-63252:773-85, Society of Petroleum Engineers Inc., presented at the 75$^{th}$ Annual Technical Conference and Exhibition, Oct. 1-4, 2000, Dallas, TX.

Vernik, "Permeability Prediction in Poorly Consolidated Siliciclastics Based on Porosity and Clay Volume Logs," Petrophysics, Mar.-Apr. 2000, 138-147.

Waxman et al., "Electrical Conductivities in Oil-Bearing Shaly Sands," *Society of Petroleum Engineers Journal* (1968) pp. 107-122.

Witt et al., A comparison of wireline and drillstern test fluid samples from a deepwater gas-condensate exploration well, SPE 56714, 1999 SPE Ann. Tech. Conf. and Exhibit., Oct. 3-6, 1999, 515-524.

Wu et al., "Inversion of multi-phase petrophysical properties using pumpout sampling data acquired with a wireline formation tester," SPE 77345, 2002 (16 pages), Only year of publication is available.

Xian Huan-Wen et al., "Upscaling hydraulic conductivities in heterogenous media: an overview", J. Hydrology 183 (1996) pp. ix-xxxii, Only year of publication is available.

Zhang et al., "Some exceptions to default NMR rock and fluid properties," SPWLA:1-14, presented at the 39$^{th}$ Annual Logging Syposium, May 26-29, 1998, Keystone, CO.

Great Britan Examination Report for Application No. GB0504935.8 dated Jun. 21, 2005.

Great Britan Examination Report for Application No. GB0606829.0 dated Sep. 8, 2006.

PCT International Preliminary Report on Patentability in Int'l Application No. PCT/US2005/000162 dated Jul. 10, 2006.

PCT International Search Report in Int'l Application No. PCT/US2004/32335 dated Aug. 29, 2005.

PCT International Preliminary Report on Patentability in Int'l Application No. PCT/US2004/32335 dated Apr. 10, 2006.

Suppl. Partial European Search Report in European Application No. 04718003.9-2315 dated Apr. 13, 2006.

Suppl. European Search Report in European Application No. 04718003.9-2315 dated Oct. 25, 2006.

PCT International Search Report for Int'l Application No. PCT/US2004/006784 dated Nov. 29, 2004.

PCT International Preliminary Report on Patentability in Int'l Application No. PCT/US2004/006784 dated Sep. 9, 2005.

PCT International Search Report for Int'l Application No. PCT/US2004/43437 dated Nov. 2, 2005.

PCT International Preliminary Report on Patentability in Int'l Application No. PCT/US2004/43437 dated Jun. 26, 2006.

EPO Supplementary European Search Report EP 02 72 5424 dated Jun. 8, 2004.

EPO Communication Pursuant to Article 92(2) EPC EP 02725424.2 dated Jan. 25, 2005.

EPO Communication Pursuant to Article 92(2) EPC EP 02725424.2 dated Oct. 12, 2005.

International Search Report PCT/US02/09819 dated Jul. 12, 2002.

International Preliminary Examination Report PCT/US02/09819 dated Nov. 15, 2002.

European Search Report for application No. 03791853.9-1234, dated Oct. 8, 2009.

\* cited by examiner

SYSTEMS AND METHODS FOR DEEP-LOOKING NMR LOGGING

CROSS-REFERENCE TO RELATED APPLICATIONS

This application is a division of U.S. patent application Ser. No. 10/837,084 filed on Apr. 30, 2004 which claims priority of U.S. Provisional Patent Application No. 60/467,568 filed on May 2, 2003 and U.S. Provisional Patent Application No. 60/508,778 filed Oct. 4, 2003, all which are incorporated herein by reference.

FIELD OF INVENTION

This patent application is directed to nuclear magnetic resonance (NMR) measurements for wireline and logging while drilling (LWD) applications. More specifically, in different aspects the application is directed to NMR systems, methods and applications for deep-looking NMR logging and directional measurement sensitivity.

BACKGROUND OF THE INVENTION

Well logging is a common practice in the oil and gas industry to evaluate underground formations for the presence and producibility of hydrocarbon reservoirs. Among the most important parameters determined in the process are the depth and thickness of formation layers containing a potential hydrocarbon reservoir, the formation porosity (i.e., the relative amount of void space in the formation), the hydrocarbon saturation (i.e., the relative percentage of hydrocarbons versus water in the pore space), and the permeability (i.e., the ability of the oil, gas, or water to flow out of the formation, into the well and eventually to the surface for recovery).

Presently, nuclear magnetic resonance (NMR) well logging is considered to be one of the most effective technique for determining these geologic parameters. NMR technology has many advantages over other logging techniques (such as gamma ray logging, sonic logging, electric logging, and others), one of the most significant being the independence of NMR measurements from formation lithology. In particular, NMR data relates in a simple manner to formation pore sizes. This relationship facilitates detection of formation fluids (i.e., gas, oil, and water) independent of the matrix mineralogy. To this end, in addition to estimation of formation porosity, hydrocarbon saturation and permeability, NMR logging enables computation of clay-bound water, capillary-bound water, and free fluid volumes, which are essential to comprehensive formation evaluation.

Generally, NMR measurements are performed as follows. A downhole static magnetic field $B_0$ is used to align the magnetic moment of spinning hydrogen (H) protons in the formation in the direction of the $B_0$ magnetic field. In order to establish thermal equilibrium, the hydrogen protons must be exposed to the polarizing field for a multiple of the characteristic relaxation time $T_1$. Then, the magnetic component of a radio frequency (RF) electromagnetic pulse polarized in a second direction orthogonal to the static field $B_0$ is used to tip the protons to align them in a third direction that is orthogonal to both the first and the second direction. This initial RF pulse is known as a 90° pulse. Following the 90° pulse the protons in the formation begin to precess about the axis of the first direction. As a result, the protons produce an oscillating magnetic field, having a frequency directly proportional to the $B_0$ field intensity at the proton's location. Due to inhomogeneities in the static magnetic field and irreversible molecular processes, the protons quickly begin to de-phase, which causes the induced signal to decay. Nevertheless, the dephasing process is partially reversible. In particular, by applying an 180° RF pulse, the instantaneous phases are reversed such that the protons gradually come back into phase, thus rebuilding the induced signal. After the signal peaks at the time when the protons are back in phase, the signal will begin to decay again due to dephasing in the opposite direction. Another 180° RF pulse can be used to again reverse the instantaneous phases and thereby rebuild the signal.

By using a series of 180° RF pulses, the signal is periodically rebuilt after each dephasing, although each rebuilding is to a slightly lesser peak amplitude due to the irreversible molecular processes so eventually it dies out completely. Each rebuilding of the signal in this manner is called a spin echo, and the time constant associated with the decay of the spin echo amplitudes is known as the transverse relaxation time $T_2$. A particular sequence of pulses, known in the art as the Carr-Purcell-Meiboom-Gill (CPMG) pulse sequence, is most frequently used. For a more comprehensive overview of the NMR technology including logging methods and various tool designs, the interested reader is directed, for example, to the book by Coates et al. entitled "NMR Logging: Principles and Applications" distributed by Gulf Publishing Company (2000), and incorporated in its entirety herein by reference for background. Additional description of NMR logging techniques is provided, for example, in U.S. Pat. Nos. 4,710,713; 4,717,876; 4,717,877; 4,717,878; 4,939,648; 5,055,787; 5,055,788; 5,212,447; 5,280,243; 5,309,098; 5,412,320; 5,517,115, 5,557,200; 5,696,448; 5,936,405; 6,005,389; 6,023,164; 6,051,973; 6,107,796; 6,111,408; 6,242,913; 6,255,819; 6,268,726; 6,362,619; 6,512,371; 6,525,534; 6,531,868; 6,541,969; 6,577,125; 6,583,621, 6,646,437 and 6,717,404, which are incorporated herein by reference.

NMR logging is typically performed using wireline tool or logging-while-drilling (LWD) tools. In the conventional wireline-logging technology, NMR logging is performed as the logging tool is being lowered into a drilled borehole. In the emerging LWD technology, the logging tools are generally rigged up as a part of the drilling string and follow a drill bit during actual well drilling. Each tool type has its own advantages. The wireline-tools enable high logging speeds and high-quality measurements. The LWD tools, on the other hand, provide real-time data during drilling operations that may be used to prevent loss of circulation, blowouts, stuck pipes, hole instability and other disastrous consequences of borehole drilling.

Yet another significant benefit of LWD technology is that it facilitates directional drilling of the borehole. Specifically, directional drilling involves the drilling of a well bore along a deviated course in order to reach a target region at a particular vertical and horizontal distance from the original surface location. This form of drilling is particularly useful for pay zone steering: a procedure in which directional drilling is used to obtain an appropriate wellbore trajectory into an oil producing formation bed (or "pay zone") based on real-time formation evaluation data and then drill substantially within pay zone boundaries. Directional drilling may be used to penetrate multiple pay zones by using fewer wells, as well as increase the borehole volume and flow rates in the pay zone.

Notwithstanding the numerous advantages of current NMR technology, present generation of NMR tools have one key weakness—shallow depth of investigation—which is typically about 10-20 cm from the tool. This is a problem because producible formation fluids (e.g., gas, oil, and water) are often displaced in the formation surrounding the borehole by invading borehole fluids (i.e., drilling mud) driven by high borehole pressure. Such invasion may occur as far as one meter into the formation with wide variations due to fluid composition, formation permeability, and applied pressure difference. As a result, conventional NMR tools having shallow depths of investigation receive signals only from the invaded section of the formation. Measurements at such shallow depths are useful to replicate porosity, $T_1$ and $T_2$ relaxation measurements, type and volume of bound fluid, and volume available for producible fluids. Because of displacement of the formation fluids, the NMR LWD systems, however, cannot accurately quantify the amounts of producible hydrocarbons (i.e., oil and gas) present in the formation surrounding the borehole—a factor of great significance in predicting producibility of a hydrocarbon reservoir.

The main obstacle to conducting deep NMR measurements is the high gradient $G_0$ of the static magnetic field $B_0$. In other words, the strength of the magnetic field $B_0$ falls off very rapidly with increasing distance from the tool. Such decrease in the magnetic field strength is primarily attributed to the magnetic configuration of the NMR tool. For instance, U.S. Pat. No. 4,350,955 to Jackson et al. ("Jackson et al.") discloses a NMR apparatus comprising a pair of cylindrical permanent magnets placed co-axially with like poles facing each other and a loop antenna placed between the magnets for transmitting and receiving radio signals. The opposing magnetic fields combine to form a toroidal region of relatively homogeneous radial static magnetic field $B_0$. The distance of the homogeneous field region from the axis of the magnets depends on the magnet dimensions and their separation. The closer are the magnets the stronger is the combined magnetic field. The magnetic field lines in the Jackson et al. design, however, disperse very rapidly in the relative proximity of the tool and therefore provide a low magnetic field gradient $G_0$ only at a distance of about 10 cm from the tool.

An improvement of the Jackson's et al. tool design is disclosed in U.S. Pat. No. 4,629,986 to Clow et al. (hereinafter "Clow et al."). Clow et al. placed a highly permeable ferromagnetic material between two permanent magnets, positioned as in Jackson's layout. This ferromagnetic material shunts more magnetic flux into the center of the tool and produces radial magnetic field lines radiating in vertical planes. Contrary to Jackson's et al. design, this configuration keeps the magnetic field lines more focused and parallel at a greater distance, which results in a stronger field $B_0$ and low gradient $G_0$ further away from the tool (i.e., about 20 cm). However, such investigation depths are still too shallow to enable adequate NMR measurements in regions of the formation unaffected by the invaded formation fluids.

Another prior art design is described, for example, in U.S. Pat. No. 6,246,236 to Poitzsch et al. (hereinafter "Poitzsch et al."), claiming priority to U.S. Pat. No. 5,977,768 to Sezginer et al., which discloses NMR tool having a low-gradient sonde and a high-gradient sonde positioned in tandem along the longitudinal axis of a tool. The '236 and '768 patents are incorporated herein by reference. The low-gradient sonde comprises two permanent magnets having separation of about 65 cm and an interposed magnetically permeable member. The configuration provides a relatively weak magnetic field $B_0'$, which has low (approximately 3 G/cm) gradient $G_0'$ that is measured at a distance of approximately 20 cm radially from the tool. The second sonde comprises two permanent magnets about 20 cm apart with an interposed magnetically permeable member. This configuration provides a stronger magnetic field $B_0''$ at approximately the same distance from the tool as the low-gradient sonde, but with greater gradient $G_0''$ (approximately 10-20 G/cm).

Each magnetic configuration in Poitzsch et al. has its own advantages. NMR measurements performed in the low gradient region, for instance, are less sensitive to the lateral motion of the tool than the measurements in the high gradient region—a characteristic useful in LWD applications, in which drill string typically undergoes severe vibrations. High field strength in high gradient region, on the other hand, provides better signal-to-noise ratio (SNR), which is very important in both wireline and LWD applications. The Poitzsch et al. tool, however, conducts NMR measurements in shallow volumes (about 20 cm deep), which are typically invaded by borehole fluids. As a result, information gathered by the tool is limited and the quality of its measurements may be compromised. Moreover, none of the above tools provide directionally sensitive data about the formation, which would facilitate directional drilling capabilities.

Sezginer et al. use a single transmitter that powers all antennas in transmit mode. That means that (a) all antennas have to be tuned to the same frequency, and (b) the interaction between antennas (mutual detuning) has to be negligible. It is not possible to suppress the mutual interaction while at the same time maintaining good azimuthal coverage. Thus, Sezginer et al. require either very narrow antennas, which have low SNR and poor azimuthal coverage or do not disclose a workable system due to the fact that antennas in close proximity are electrically equivalent to coupled tank circuits, which exhibit split resonances. The prior art does not disclose or suggest a system that obtains directional information from a formation and also is capable of operating at multiple frequencies.

Accordingly, it is an object of the present invention to provide a NMR tool suitable for comprehensive evaluation of underground formations during wireline or LWD operations. In particular, it is an object of the invention to enable NMR measurements in deep regions of the formation that are substantially free of borehole fluids invasion. Another object is to enable both shallow and deep measurements using a single magnetic assembly. Yet another object of the invention is to provide NMR tool having directional sensitivity and suitable for directional drilling based on directionally sensitive NMR measurements. A further object of the invention is to provide an NMR pulse sequence that minimizes the tool's power consumption, while maximizing the SNR of deep NMR measurements.

SUMMARY OF THE INVENTION

This application is directed in one aspect to NMR tools capable of conducting NMR measurements in deep sensitive volumes, where borehole fluid effect can be ignored for practical purposes. In another aspect, the application is directed to NMR tools having directional sensitivity. The tool is capable of producing azimuthally symmetric static magnetic field $B_0$ with a low gradient $G_0$, which facilitates greater depths of investigation. In a specific embodiment, NMR measurements can be conducted in a plurality of sensitive volumes ranging from about 20 cm to about 80 cm and beyond from the tool. Shallow volumes may be used to replicate the conventional NMR logging measurements, such as porosity, $T_1$ and $T_2$ relaxation measurements, bound fluid volume, etc. These measurements characterize the pore space, the type and volume of bound fluids and volume available for producible (movable) fluids. Deep volumes enable quantification of hydrocarbon saturation substantially independent of the borehole effects, such as formation invasion by borehole fluids. To this end, the deep measurements may be used to supplement the shallow free-fluid measurements by quantifying the amount of oil and gas present at a distance from the borehole. Taken together, shallow and deep volume measurements may be used as basis for stand-alone formation evaluation, enabling more accurate estimates of porosity quantification of producible hydrocarbons, for borehole invasion profiling, and others.

In a preferred embodiment, the NMR tool comprises two permanent magnets polarized along a longitudinal axis and aligned with like poles facing each other. One or both poles of each magnet are extended longitudinally with one or more pole pieces. Pole pieces used in this application have high permeability to intensify the static magnetic field of the magnets and make it more homogeneous in the formation region surrounding the space between the magnets. Interposed between the inner set of poles is an RF antenna assembly.

There are several possible implementations for the antenna assembly in accordance with different embodiments. By way of illustration, such an assembly comprises a plurality of independently addressable antenna segments. The antenna segments can be implemented as coils that may be wound around a magnetic core or saddle antenna pieces. In various embodiments the antenna segments may be disposed about a suitable reference axis, such as the tool axis, which usually is substantially parallel to the borehole axis. Preferably, when so disposed, the antenna segments are distributed symmetrically. This results in dividing the addressable sensitive volume sections in the formation in a regular manner. However, this preference is not intended as a limitation. In preferred embodiments, either three or four antenna segments are disposed about such an axis. Alternatively, the antenna assembly comprises a tubular ferromagnetic core and three coils wound around the core. The coils include at least one solenoid and at least two orthogonally-placed saddle coils. The antenna assembly is enclosed into a non-conductive, non-magnetic shield, which protects it from the borehole environment. Finally, the entire magnetic assembly may be mounted on a drill collar having mud flow conduit therein to facilitate mud circulation in the borehole.

In another embodiment, the NMR tool comprises a single, axially polarized magnet assembly having a permanent magnet longitudinally extended, at both poles, with one or more soft-magnetic pole pieces, thus simulating a magnetic monopole in the near regions of the formation. One or both pole pieces may in turn be adjacent to one or more RF antenna assemblies. Each antenna assembly further comprises a (tubular) ferromagnetic core and one or more antenna coils wound around the core. The coils include preferably at least one solenoid coil and at least two orthogonally-placed saddle coils. Each antenna assembly is enclosed into a non-conductive, non-magnetic protective shield. Finally, the entire magnetic assembly may be mounted on a drill collar having mud flow conduit therein to facilitate mud circulation in the borehole.

In a preferred embodiment, the NMR tool is capable of directional NMR detection. In particular, the directional sensitivity of the tool is provided by a unique design of RF transceiver antenna and a novel data processing method. In particular, a solenoid coil is capable of imparting an azimuthally symmetric magnetic field $B_1$. Directionally-sensitive antenna segments, in turn, are capable of detecting NMR signals from different sections of the sensitive volume. The data processing method in a preferred embodiment combines NMR signals detected by the antenna coils to enable analysis of the received NMR signals to determine which regions of formation are characterized by the given NMR response. Such directional NMR detection, combined with conventional accelerometer and magnetometer readings, enables real-time payzone steering during borehole drilling.

In another aspect, this application is directed to a method for optimizing the reception of signals from a deep sensitive volume of the tool with reduced power requirements. The method is based on a novel pulse sequence for NMR relaxation measurements. In particular, by lengthening each refocusing pulse ($\pi$) of the standard CPMG pulse sequence and frequency-modulating each pulse, a substantial improvement in signal-to-noise ratio (SNR) results, thus improving the quality of deep NMR measurements. In another aspect, various signal-processing techniques are disclosed suitable to further improve SNR from deep measurements. Additional aspects of the invention(s) in this disclosure will become apparent to those skilled in the art upon reviewing the description in light of the illustrative figures described below.

BRIEF DESCRIPTION OF THE DRAWINGS

Advantages of the technical approaches disclosed in this patent application will become apparent from the following description of the accompanying drawings. It is to be understood that the drawings are to be used for the purpose of illustration only, and not as limitations on the scope of the attached claims.

DETAILED DESCRIPTION

The Magnetic Assemblies

Figure 2:
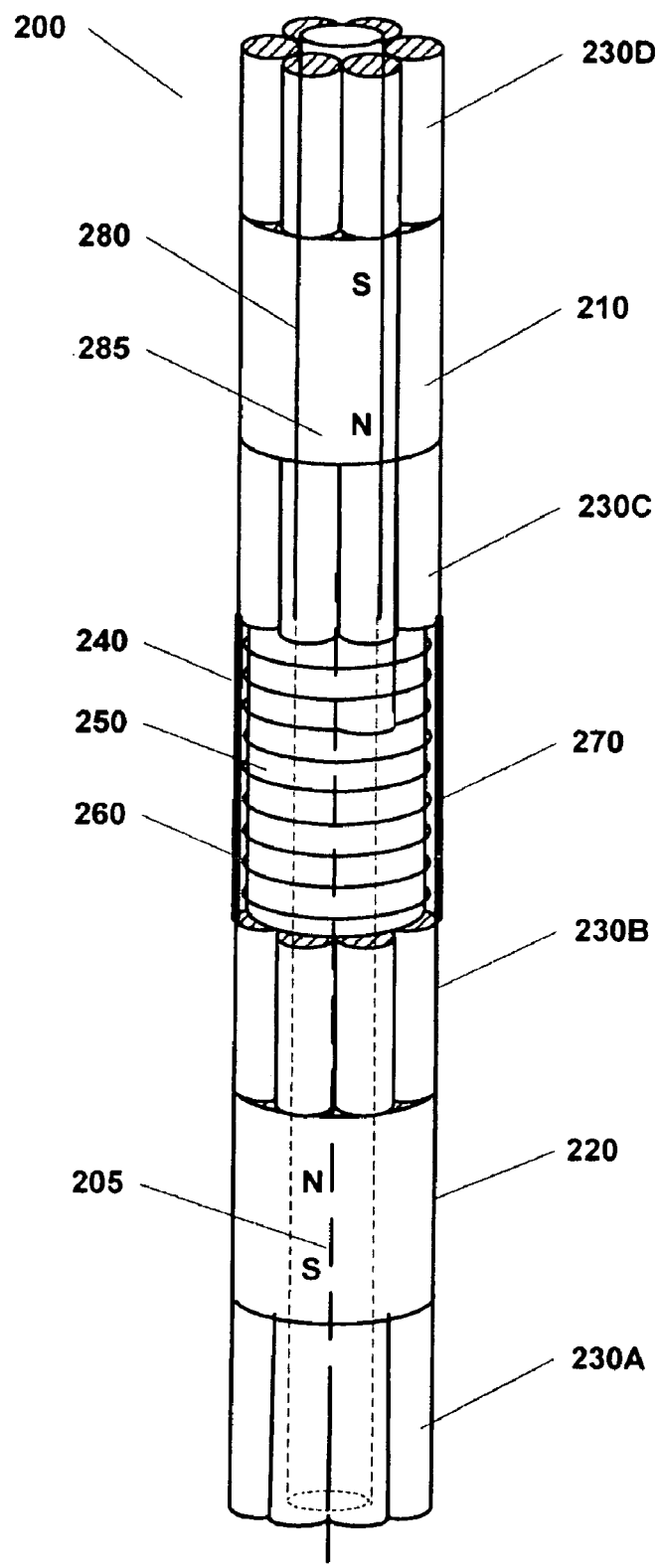
FIG. 2 is schematic diagram of the magnetic assembly of the NMR tool in accordance with a preferred embodiment.

FIG. 2 illustrates a preferred embodiment of an NMR tool, which is suitable for logging-while-drilling of a geologic formation. Tool 200 comprises the following components: two magnetic configurations each comprising a permanent magnet (magnets 210 and 220) positioned with like poles facing each other and a plurality of pole pieces 230A, 230B, 230C, and 230D (subsequently referred to as pole pieces 230), longitudinally extending one or both poles of a magnet. Interposed between the magnetic configurations is a RF transceiver antenna assembly 240, which comprises a soft-magnetic core 250 and a plurality of coil windings 260. Antenna assembly 240 is preferably surrounded by a protective shield 270. All aforementioned components are centered along longitudinal axis 205 of tool 200, which in several coincides with longitudinal axis of the borehole. In LWD embodiments, tool 200 is mounted within a tubular drill collar (not shown) having mud flow conduit 285 therein to facilitate mud circulation in the borehole.

(1) Magnets

Figure 3A:
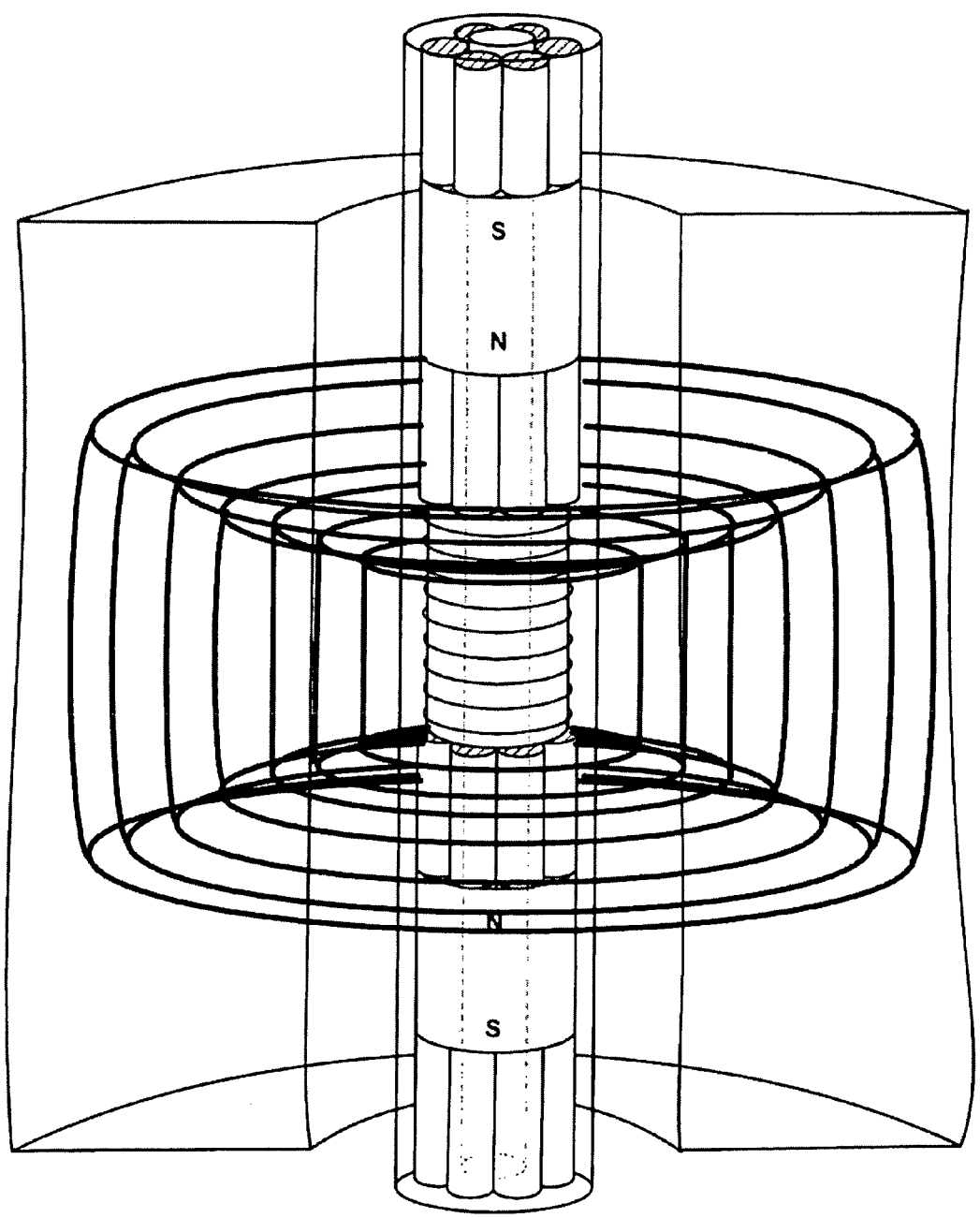
FIG. 3A-3D provide various views of the static magnetic field flux lines, oscillating magnetic field flux lines, and sensitive volumes generated by the NMR tool of the embodiment illustrated in FIG. 2.
Figure 3B:
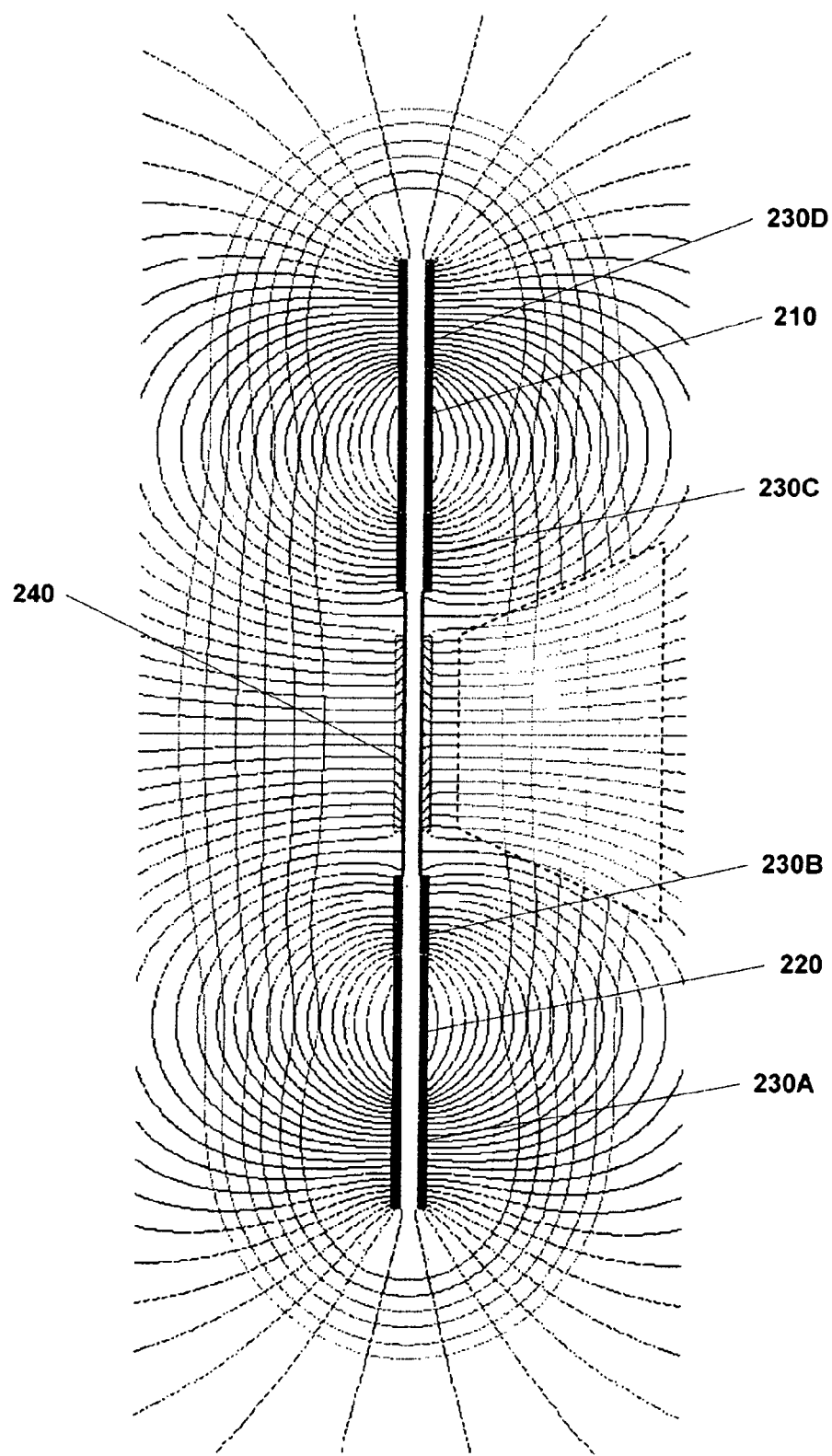

With reference to FIG. 2, in accordance with a preferred embodiment, magnets 210 and 220 are cylindrical magnets having a substantially circular cross section, each magnet being generally elongated and centered along the longitudinal axis 205 of the magnetic assembly 200. In operation, this axis is usually aligned with the axis of the wellbore. Magnets 210 and 220 are preferably polarized in a direction parallel to the longitudinal axis of the magnetic assembly 200 and mounted with like magnetic poles facing each other. For each magnet 210 and 220, the magnetic field lines travel as shown in FIG. 3B. As shown, in the region between the magnets, the magnetic field lines extend radially in all azimuthal directions to create a static field $B_0$ in a substantially cylindrical region of the formation surrounding the borehole, as also shown in FIG. 3A. Because of the separation, the magnitude of the static magnetic field $B_0$ in the region between magnets 210 and 220 (in the vicinity of any given radius) is substantially homogeneous.

Magnets 210 and 220 are preferably strong Alnico magnets with remanence induction of approximately 1.25 Tesla. Alnico magnets are composed primarily of alloys of Aluminum, Nickel, and Cobalt. Alnico materials are generally characterized by excellent stability over a wide temperature range, high residual induction, and relatively high energies. Such magnets are manufactured through either a casting or sintering process. Cast magnets may be manufactured in complex shapes, in a preferred embodiment magnets 210 and 220 are tubular (i.e., rod-shaped). It should be noted that sintered Alnicos offer slightly lower magnetic properties but better mechanical characteristics than cast Alnicos. For most practical purposes, either manufacturing method is suitable.

For optimized performance, the length of the magnets is preferably about 4-5 times of the diameter. To this end, in a preferred embodiment, magnets 210 and 220 are preferably about 13 cm in diameter and approximately 60 cm long. It should be understood by those of skill in the art that the length of the magnets may vary depending on the specific design needs, provided of course that the magnet's length-width ratio is selected to optimize its performance. The above-described Alnico magnets are manufactured, for example, by the Alnico Products Division of Group Arnold, magnetic products group of SPS Technologies, Inc. based in Marengo, Ill.

In alternative embodiments, magnets 210 and 220 may comprise permanent magnets, such as hard ferrite (SrO-6 ($Fe_2O_3$)) magnets having strontium carbonate and iron oxide composition, neodymium-iron-boron (NdFeB) magnets, or samarium cobalt (SmCo) magnets. In other embodiments, magnets 210 and 220 may comprise electromagnets that are made of thin-gauge copper or aluminum foils. Furthermore, the shape of magnets 210 and 220 may vary depending on the specific design need, for example, it may be a solid cylinder or a cylindrical annulus (i.e., tubular). In different embodiments, magnets may be integral, or may comprise a plurality of smaller magnets bonded together. In the latter design case, magnetization direction of each smaller magnet may vary as long as total magnetic moment is aligned longitudinally with the axis of the magnetic configuration 200 and like poles of magnets 210 and 220 face each other. The above-described magnets and variations thereof are can be made, for example, by Group Arnold, magnetic products group of SPS Technologies, Inc. based in Marengo, Ill.

(2) Pole Pieces

In accordance with a preferred embodiment, magnets 210 and 220 are extended at one or both poles by a plurality of pole pieces 230 (see pole pieces 230A, 230B, 230C, and 230D in FIG. 2). A pole piece in this application is a piece of (ferromagnetic) material attached to one end of a magnet and so shaped that the distribution of the magnetic flux in the adjacent medium is appreciably controlled. Pole pieces 230 are composed of high permeability material, preferably greater than about 100. Suitable materials for the pole pieces may comprise iron, permeable steel or other soft-magnetic alloy of iron and nickel. In the specific embodiment discussed above, pole pieces are cylindrically shaped rods about 30 cm long (which may vary depending on the specific design requirements). Pole pieces 230 may be attached to a magnet pole face by adhesive bonding or with studs or bolts. For greater efficiency, a non-magnetic gap between the magnet poles and the pole pieces 230 should be as minimized, and preferably made as small as practically possible. While the pole pieces can be allowed to carry some load, the connection between pole pieces 230 and magnets 210 and 220 should be done in a manner that minimizes the structural load on the magnets.

In one aspect of the invention, pole pieces 230 shape the static magnetic field $B_0$ generated by magnets 210 and 220. With reference to FIG. 3B, for each magnet 210 (220), the magnetic field lines travel outward from an end of the magnet through the respective inner set of pole pieces 230 and into the formation, and travel inward to the other end of the magnet. In general, pole pieces 230 make the magnetic field intensity more uniform and homogeneous in the annular regions of the formation surrounding the borehole.

To this end, in accordance with a preferred embodiment, the longitudinal separation between the inner pole pieces of magnets 210 and 220 is about 80 cm. The amount of separation between magnets 210 and 220 is determined based on several factors, including: (1) selecting the requisite magnetic field strength; (2) received depth of investigation; and (3) generating a field having small radial variations in the region of interest so that the echoes received during a pulse sequence are less sensitive to lateral tool motion. In general, as the separation between magnets 210 and 220 decreases, the magnetic field becomes stronger and less homogeneous. Conversely, as the separation between magnets 210 and 220 increases, the magnetic field becomes weaker and more homogenous.

Figure 3C:
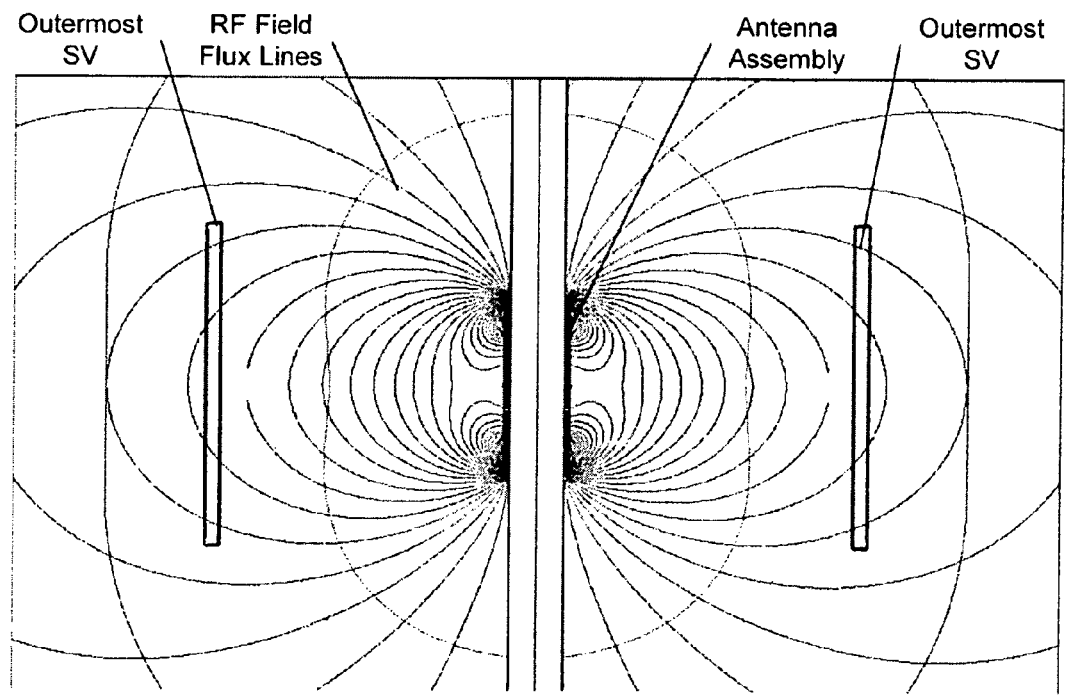
Figure 3D:
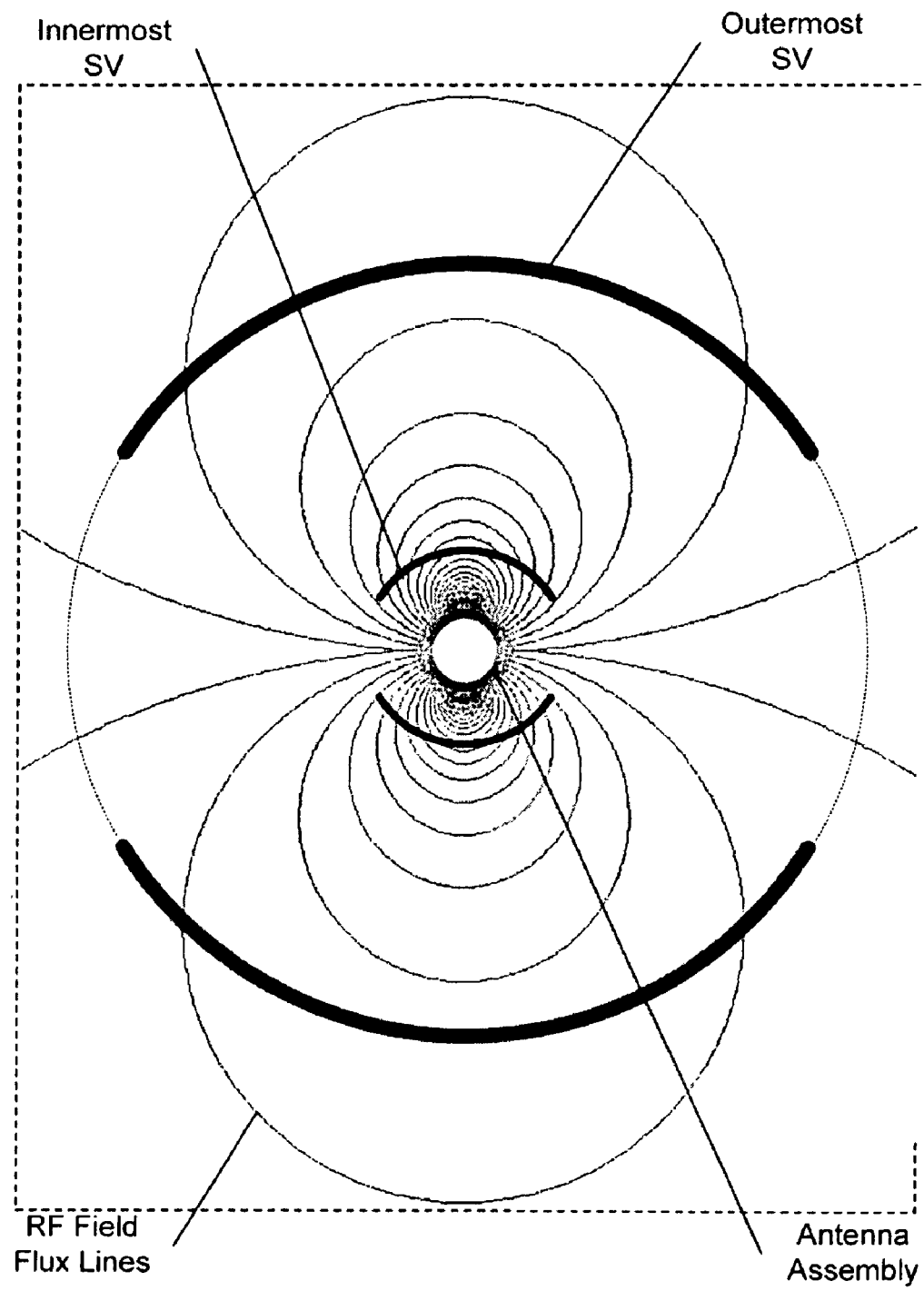
Figure 3E:
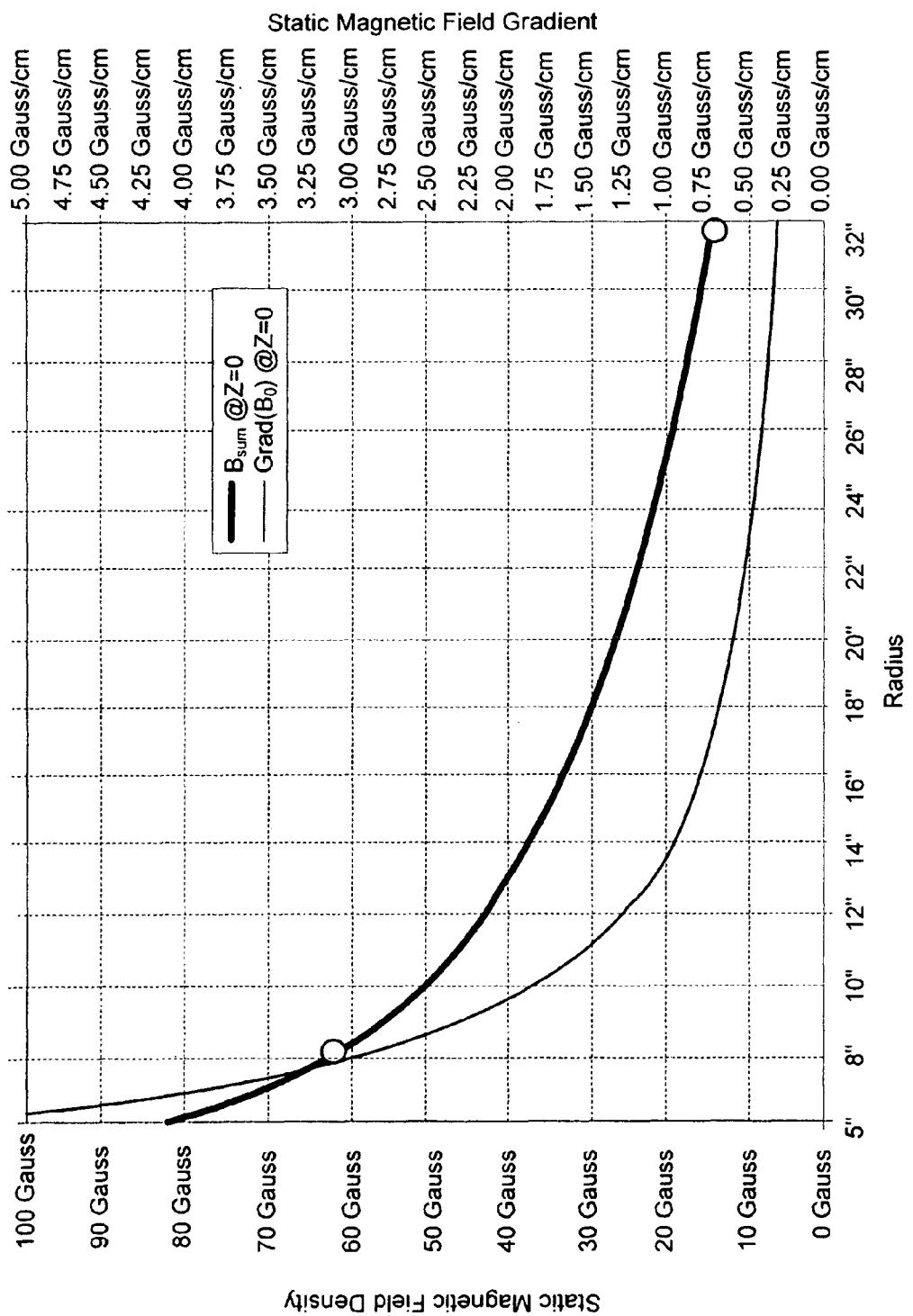
FIG. 3E illustrates the distribution of the static magnetic field strength and static magnetic field gradient as a function of distance from the tool.

FIG. 3E illustrates how the field strength ($B_0$) and field gradient ($G_0$) of the static magnetic field change as functions of radius (R) from the tool in accordance with a preferred embodiment. It can be seen from FIG. 3E that magnetic assembly 200 provides higher field strengths and lower field gradients further away from the tool than prior art NMR tools. In particular, magnetic assembly 200 imparts an azimuthally symmetric static magnetic field $B_0$ suitable for measuring NMR signals in a region extending 20 cm away from the tool to about 80 cm and beyond into the formation, in some instances about 1 meter deep. For instance, prior art discloses field strengths of about 10 G or lower at a distance of 30 cm from the tool. In contrast, an embodiment of the tool in accordance with the principles disclosed in this application shows field strength of over 10 G at 80 cm or more away from the tool.

Figure 18:
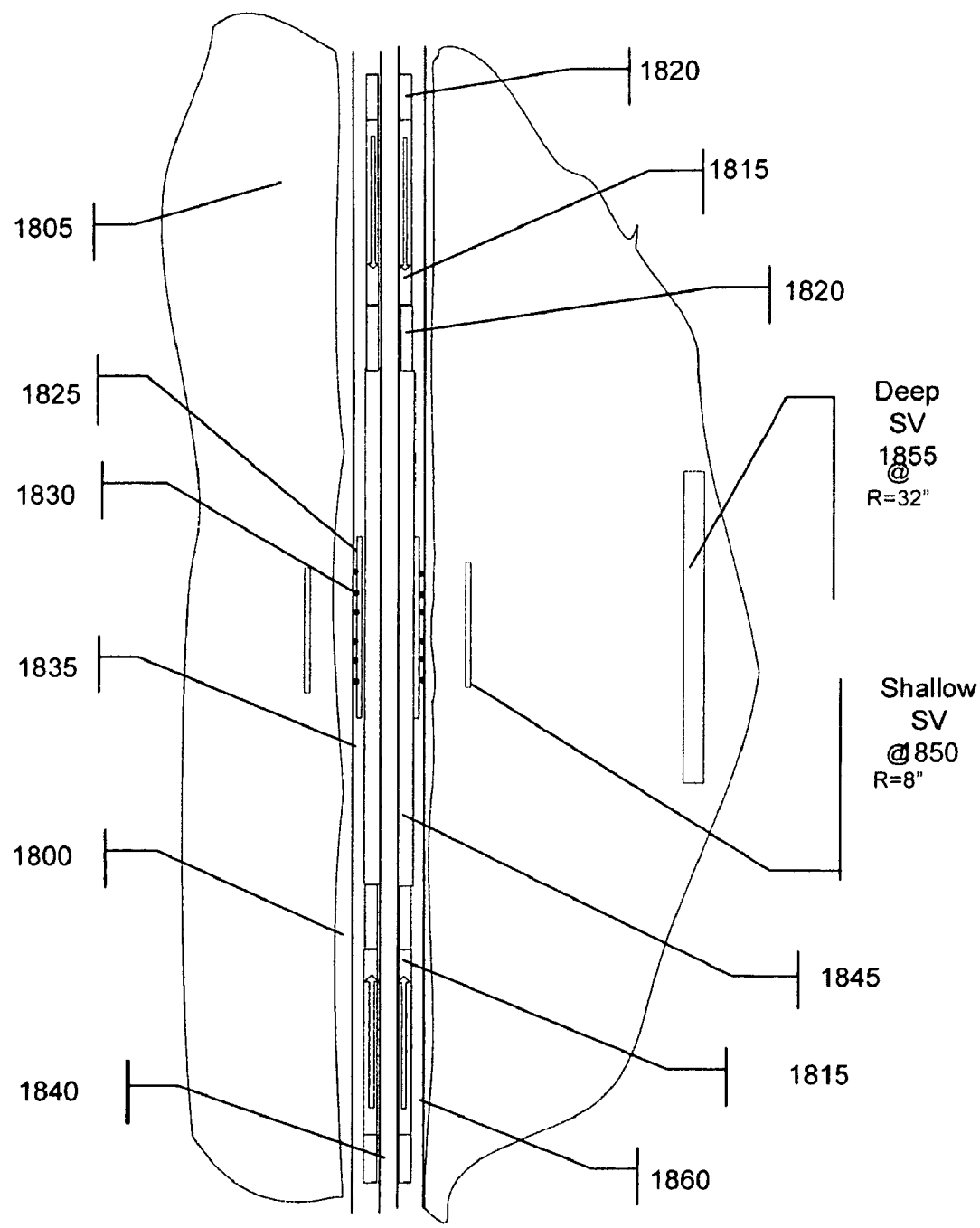
FIG. 18 provides an illustration of a general logging tool, including in a logging while drilling context.

A general structure of the logging tool in a specific embodiment is shown in illustrative FIG. 18. Borehole 1800 in formation 1805 has logging tool 1810 comprising magnet 1815 with pole piece 1820. Antenna core 1825 has antenna coils 1830 with the antenna assembly protected by antenna sleeve 1835. The antenna is mounted on yoke 1845. In operation, the deep looking logging tool is able to collect data from shallow sensitive volume 1850 and deep sensitive volume 1855. The entire magnet and antenna assembly may be mounted on a drill collar 1860 in a LWD application. Also shown is flow channel 1840, which is important for use of the logging tool 1810 while drilling to allow mud to flow to the drill bit.

Alternative Magnet Design Construction

It should be noted that the embodiment described in FIG. 2 with two opposed magnets, although preferred, may be replaced to a good approximation by a single magnet with pole extended by pole pieces. The shaping of the magnetic flux lines by pole pieces even in the absence of opposing poles provides a substantially radial magnetic field in a portion of the formation surrounding a borehole. Thus, useful NMR data may be obtained for sensitive volumes in the vicinity of a logging tool with a single permanent magnet having pole pieces. This simplifies the construction of a suitable magnet that provides a good approximation to magnetic flux lines directed outwards in a substantially radial direction.

Figure 4A:
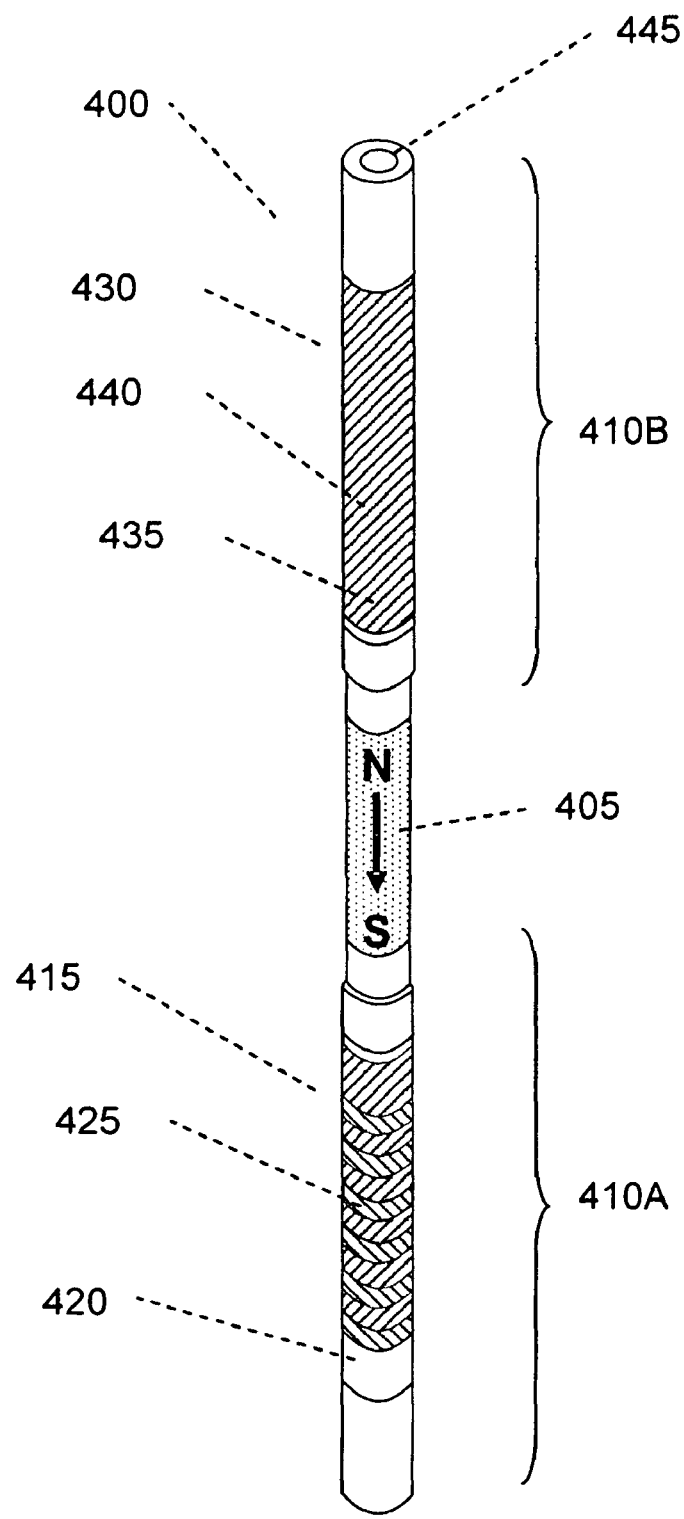
FIG. 4A is schematic diagram of the magnetic assembly of the NMR tool in accordance with a second embodiment.
Figure 19:
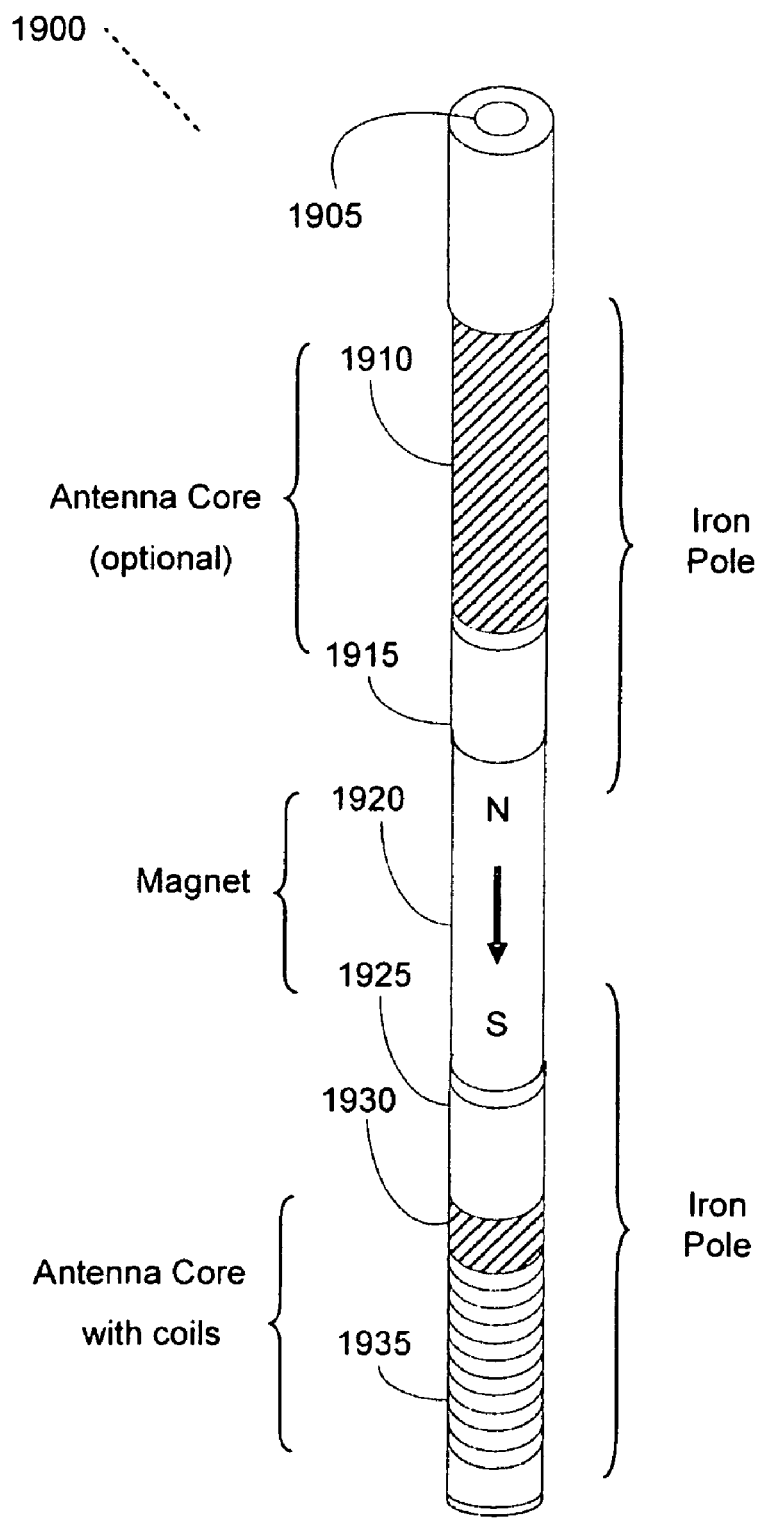
FIG. 19 shows an illustrative magnetic system, suitable for deployment in a borehole, with a single magnet and two attached soft magnetic poles, which system is suitable for generating substantially radial magnetic flux lines in a region of a formation about the magnetic system.

One such embodiment of a NMR tool is shown in FIG. 4A. Tool 400 comprises a single permanent magnet system having a tubular, axially polarized magnet 405 and one or more soft-magnetic pole pieces 410A and 410B extending the poles of magnet 405. Tool 400 further comprises a RF transceiver antenna 415 surrounding one or more pole pieces 410A. Antenna 415 comprises antenna core 420 and one or more antenna coils 425 wound around core 420. Tool 400 may further comprise another antenna 430 surrounding one or more pole pieces 410B. Antenna 430 may also comprise antenna core 435 and one or more antenna coils 440. Finally, tool 400 is mounted on a tubular drill collar 445 having a mud flow channel therein. FIG. 19 shows another view of the magnet configuration in this embodiment. In particular, logging tool 1900 has central channel 1905, optional antenna core 1910 adjacent to pole piece 1915 extending a pole of magnet 1920. The other pole of magnet 1920 is extended by pole piece 1925, which is adjacent to core 1930 with wound coil 1935 forming an antenna. As indicated, a pole piece, preferably iron, may be used doubling as an antenna core and pole extender.

The magnetic components of the tool 400 are preferably made of substantially similar materials and have substantially similar magnetic and electrical characteristics as the corresponding components in the tool 200 of the embodiment, which was described above.

Figure 4B:
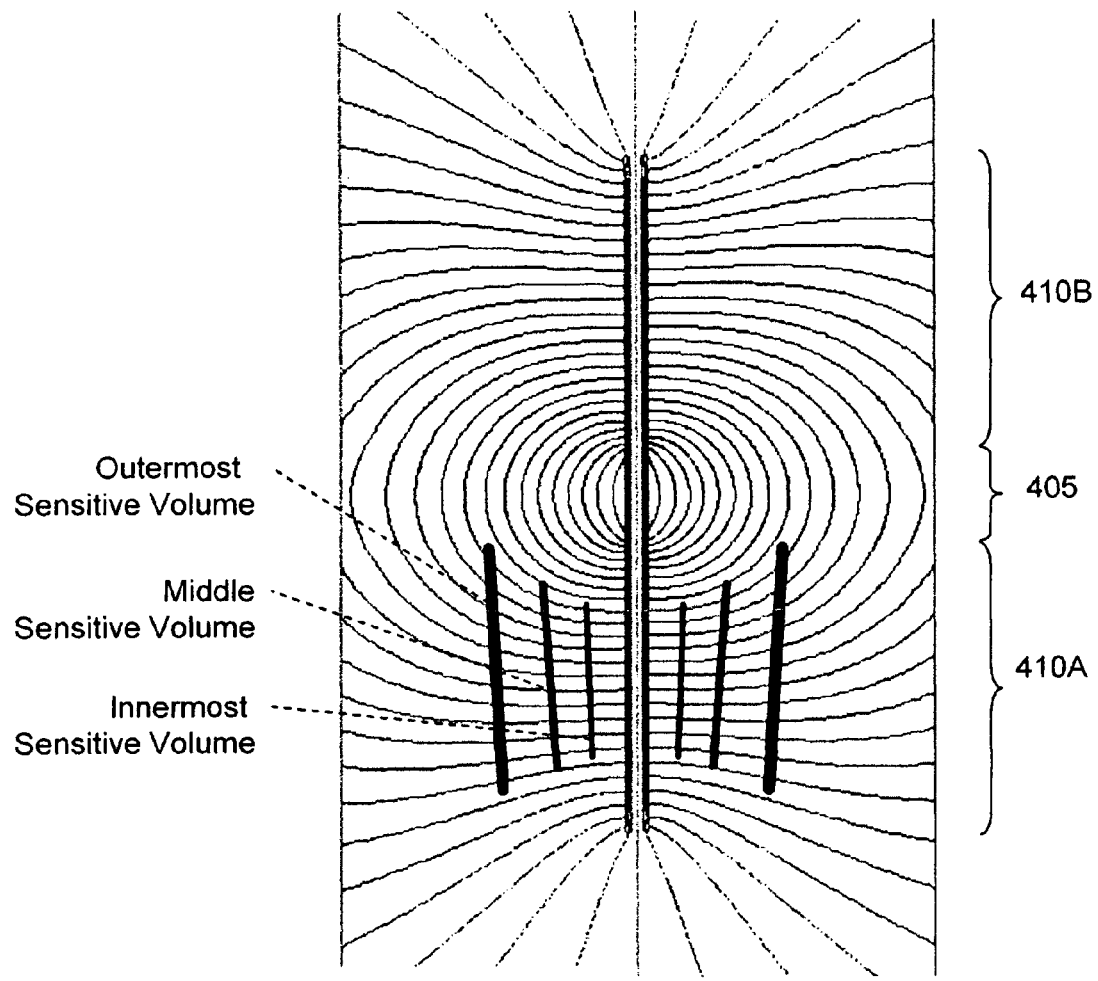
FIG. 4B illustrates static magnetic field flux lines and sensitive volumes generated by the NMR tool of the second embodiment.

FIG. 4B shows the flux lines of the NMR tool 400. The tool 400 creates two sets of the sensitive regions suitable for NMR measurements. The two sensitive regions are located in front of upper and lower soft magnetic poles 410A and 410B. In these regions, the direction of the static field is substantially radial. In FIG. 4B, only one region of the nested sensitive volumes (SV) is denoted in front of the pole pieces 410A. The shapes of the sensitive volumes are different from ideal cylinders and their boundaries are not exactly parallel to the tool's axis.

Antenna Assembly in the First Embodiment (1) Yoke

In accordance with a one embodiment, the proximal ends of the inner pole pieces 230 are attached to a yoke (not shown). The yoke may have cylindrical shape with its longitudinal axis aligned in coincidence with the axis of the tool 100. Preferably, pole pieces 230 are not joined rigidly with the yoke, but can move some against each other to provide overall bending flexibility. Because the yoke is interposed between the inner pole pieces of magnets 210 and 220, the entire magnetic assembly is symmetric around the yoke. The length of the yoke is preferably about 80 cm. Thus, the length of the entire magnetic assembly in this embodiment is about 315 cm. In general, the yoke may provide support for RF transceiver antenna 240, as described next. The yoke is preferably made of a mechanically durable soft-magnetic material.

(2) Antenna Core

With reference to FIG. 2, in accordance with a preferred embodiment, magnetic assembly 200 further includes transceiver antenna 240 mounted on the yoke or directly on drill collar 280. Transceiver antenna 240 comprises antenna core 250 and coil windings 260. Core 250 is preferably shaped as an annular cylinder with drill collar 280 (or yoke) passing through the longitudinal cavity extending within core 250. The total length of core 250 is about 72 cm. In a preferred embodiment, core 250 preferably comprises several rings stacked on a drill collar (or yoke) 280. The rings are preferably made of soft-magnetic material having high magnetic permeability. The soft-magnetic rings may be made from soft ferrite, ferrite polymer composites, powdered iron or nickel cores, etc.

In a preferred embodiment, core 250 has magnetic permeability of about 100. It is important that the core material maintains its permeability to limit RF power losses and does not saturate due to the static magnetic field $B_0$ generated by magnets 210 and 220. It will be appreciated that the permeability values of core 250 may vary depending on the specific design requirements.

In conjunction with pole pieces 230, core 250 shapes the static magnetic field generated by magnets 210 and 220 in the sensitive region. With reference to FIGS. 3B and 3C, core 250 enables even and azimuthally symmetric distribution of magnetic field lines along its entire length. As a result, magnetic field intensity is distributed evenly along core 250, which makes the static magnetic field $B_0$ more uniform in a plurality of sensitive volumes extending as far as one meter into the formation surrounding the borehole, as shown in FIG. 3A.

(3) Antenna Coils

Figure 5:
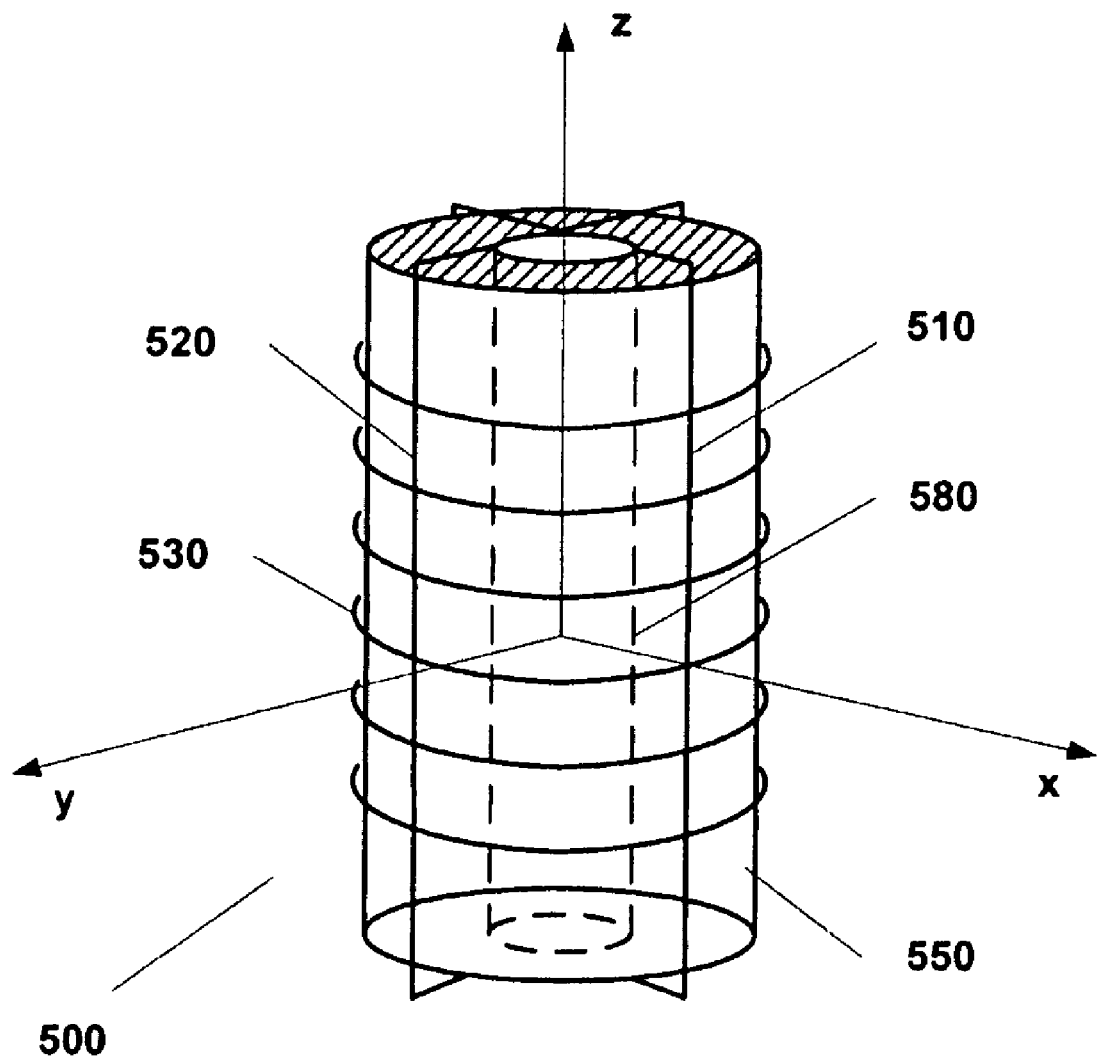
FIG. 5 is an elevated view of a transceiver antenna assembly in a preferred embodiment.

With reference to FIG. 5, in a preferred embodiment, RF transceiver antenna assembly 500 comprises at least three coil windings 510, 520, and 530 wound around antenna core 550 (corresponding to core 250 in FIG. 2). Antenna coils 510 and 520 are preferably saddle coils, each having one or more windings. Saddle coils 510 and 520 are preferably rotated 90° with respect to each other along the longitudinal axis of the tool (z-axis in FIG. 5), so that coil 510 is substantially co-planar with the x-axis, and coil 520 is substantially co-planar with the y-axis. Antenna coil 530 is a solenoid, preferably having a plurality of windings lying in planes substantially orthogonal to the longitudinal axis of the tool. In a preferred embodiment, solenoid coil 530 comprises eight-windings having total inductance of about 27 µH. In alternative embodiments, two or more solenoid coils having different inductances may be used.

In an important aspect of the novel approaches in this application, antenna 500 is suitable for azimuthally symmetric and directionally sensitive NMR signal detection. In particular, during transmission, the transmitter output signal may be routed to either one of the coils. In a preferred embodiment, solenoid coil 530 is used to impart RF field $B_1$ orthogonal to the static field $B_0$ in the entire sensitive volume, whereas saddle coils 510 and 520 are used to impart RF field $B_1$ orthogonal to the static field $B_0$ in restricted sections of the sensitive volume. During reception, the NMR signals from all three coils are preferably detected, amplified, and processed, as discussed below. It should be noted that coils 510, 520, and 530 may be combined in a plurality of configurations for transmitting RF pulses and for receiving NMR signals from shallow and the deep volumes. Moreover, two or more solenoid coils having different lengths (i.e., number of windings) may be used to excite NMR signals in shallow and deep volumes.

To achieve azimuthally symmetric nuclear magnetic resonance in the surrounding formation, a solenoid coil 530 is preferably used. When RF power pulses are conducted through solenoid coil 530, the coil generates an RF equivalent magnetic dipole centered at the origin and directed along the z-axis, as shown in FIG. 3C. The equivalent magnetic dipole generates an RF magnetic field directed opposite to the dipole direction and of substantially equal amplitude within a sensitive volume in the formation (the sensitive volume is a cylindrical shell with thickness determined by the bandwidth of the RF pulse). Since axially-oriented $B_1$ field lines are substantially orthogonal to the radially-oriented static magnetic field $B_0$ in all azimuthal directions, the nuclear magnetic resonance is induced in the entire sensitive volume.

Saddle coils 510 and 520 can be used in a specific embodiment to achieve azimuthally focused nuclear magnetic response in the surrounding formation. When RF power pulses are conducted through saddle coils 510 and 520, they produce RF dipole in a direction transverse to the longitudinal axis of the tool. Unlike solenoid coil 530, saddle coils 510 and 520 generate radially-oriented $B_1$ field lines orthogonal to the static field $B_0$ along their respective planes. (This characteristic is exploited to provide directional sensitivity to the antenna 500, as discussed below.) Thus, in a vertical borehole, for example, saddle coil 510 may be sensitive in the east-west direction, while saddle coil 520 may be sensitive in the north-south direction as indicated in FIG. 3D.

It should be noted that core 550 significantly improves the efficiency of RF antenna 500 by offsetting the reduction in the antenna aperture due to the presence of conductive drill collar 580 (or yoke). In particular, coil windings of antenna 500 are magnetically coupled to ferromagnetic core 550 such that, when the electrically conductive coils 510, 520, and 530 are energized with AC current, a magnetic dipole of increased magnetic moment is formed in core 550, thereby increasing the strength of RF magnetic field $B_1$. As a result, antenna 500 is capable of generating a much larger magnetic moment than typical nonmagnetic-cored antenna, for the same power input. In the absence of antenna core 550, large eddy currents would be induced in drill collar 580 (or yoke), which would tend to oppose the antenna currents and would result in significantly reduced sensitivity during reception, and in much larger current and power requirements during transmission.

The illustrative antenna of the first embodiment is but one of many possible antenna configurations. Some illustrative examples of directional antennas including those using combinations of multiple solenoids are described next.

Alternative Antenna Assembly Embodiments (1) Yoke

Figure 7:
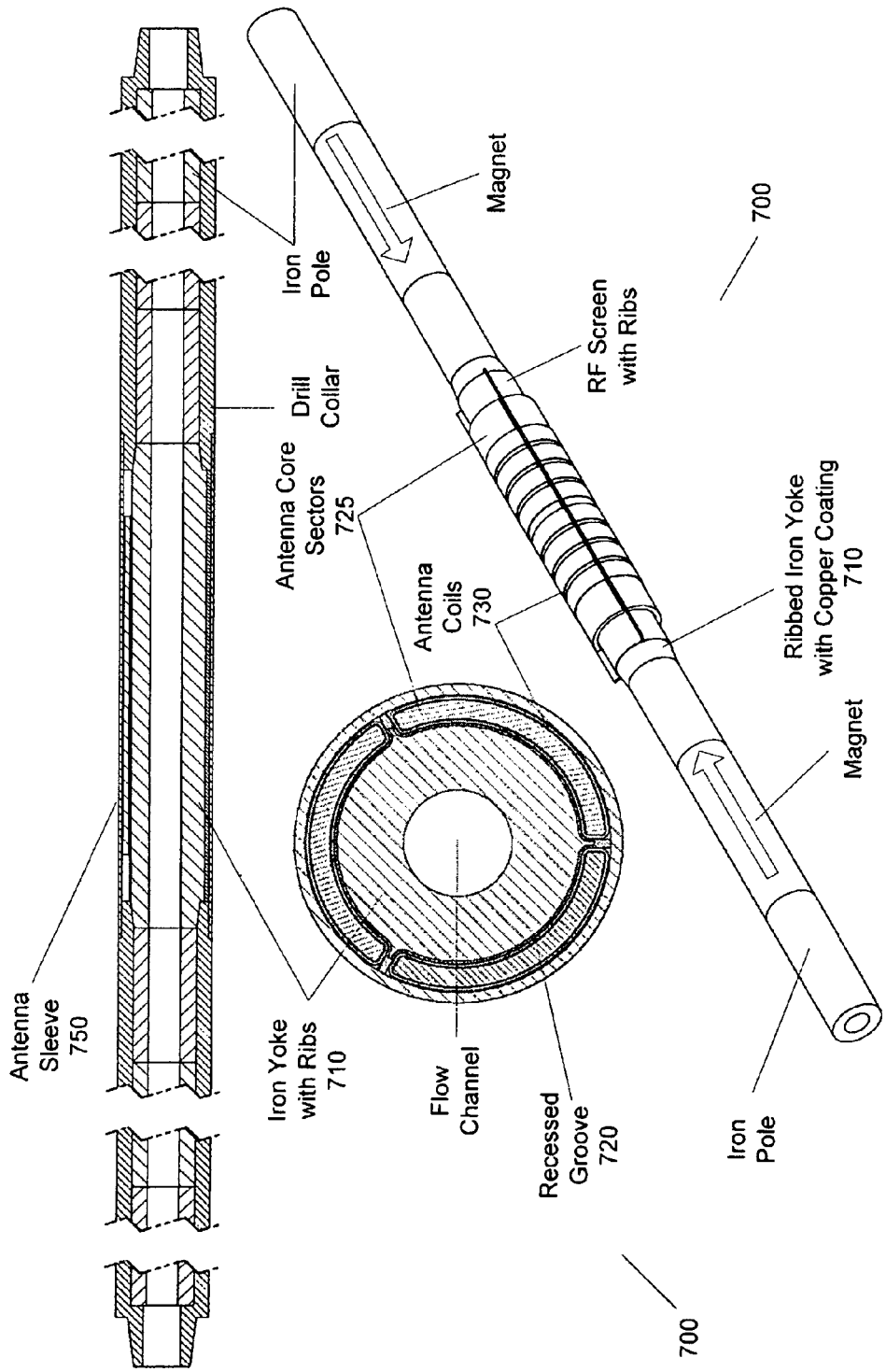
FIG. 7 shows sectional and elevated views of the transceiver antenna assembly in accordance with a second embodiment.
Figure 7A:
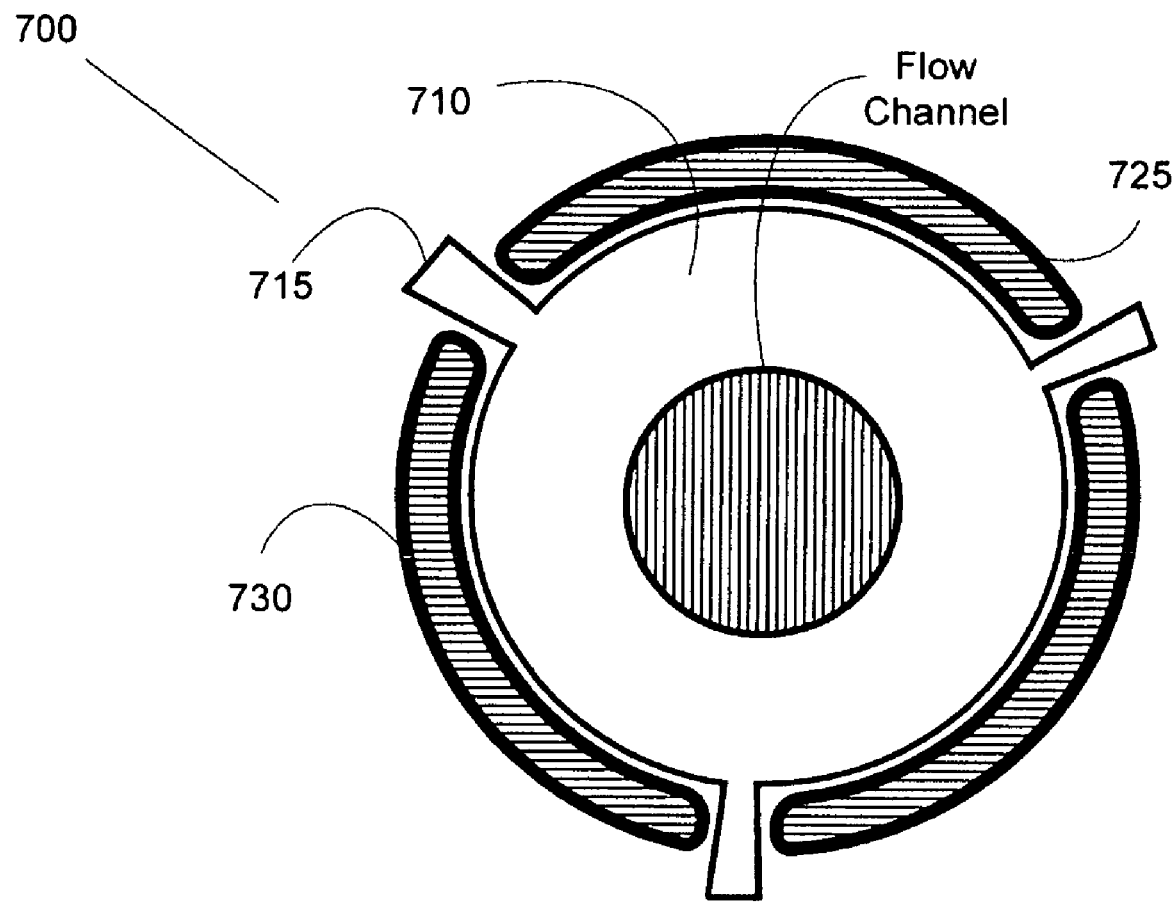
FIG. 7A shows a cross-sectional view.

With reference to FIG. 7, the antenna assembly 700 in accordance with a second embodiment is set on a ribbed yoke 710. The yoke 710 has a plurality of guide projections 715, which are formed along its outer surface. The guide projections 715 extend outwardly away from opposite sides of yoke 710, as illustrated, and are spaced apart from one another at a predetermined interval along the longitudinal extent of yoke 710. Guide projections 715 are positioned to form two or more spaced-apart rows of guide projections along each side of yoke 710, with each row extending along the length of yoke 710. In a specific embodiment, three guide projections are formed on the surface of yoke 710, thereby creating three spaced-apart rows. As a result, three generally centrally positioned grooves or recessed region 720 are provided along the outer periphery of yoke 710, extending along of the sides of yoke 710, as well as along the opposite ends of yoke 710.

The surface of yoke 710 is preferably coated with copper, which provides an RF screen. Within the gaps between adjacent coils, the copper screen can be extended up to the inner diameter of the antenna sleeve 750, which preferably encloses the entire antenna assembly 700, to reduce the magnetic coupling between antenna coils 730. The radial extension of the RF screen in the space between the adjacent coils 730 allows for correction of the RF field pattern close to the tool. For the deep-looking tool, the air gap between core segments 725 has insignificant influence on the field variations within the deep sensitive volume.

(2) Antenna Core

With reference to FIG. 7, antenna assembly 700 in accordance with a second embodiment comprises two or more core segments 725 adjacent to yoke 710 and extending longitudinally within recessed regions 720 along the surface of yoke 710. The shape of each core segment 725 resembles a sector of a tubular cylinder cut along its longitudinal axis. Core segments 725 are separated from each other by guide projections 715 of yoke 710.

Core segments 725 are preferably made of soft-magnetic material(s) having high magnetic permeability. The soft-magnetic core sectors 725 may be made from soft ferrite, ferrite polymer composites, powdered iron or nickel cores, or others. In a preferred embodiment, core 725 has magnetic permeability of about 100. It is important that the core material maintains its permeability to limit RF power losses and do not saturate due to the static magnetic field $B_0$ generated by the magnetic assembly (not shown). It should be understood that the permeability of core 725 may be different depending on the specific design requirements. It is desirable, however, that all core sectors 725 be made of the same material and have the same permeability.

(3) Antenna Coils

Antenna assembly 700 further comprises a plurality of antenna coils 730 wound around core segments 725. In particular, each core segment 725 carries at least one antenna coil 730. Each antenna coils 730 resembles a deformed solenoid. Each coil 730 preferably has a plurality of windings lying in planes substantially orthogonal to the longitudinal axis of the tool. In a preferred embodiment, each coil 730 comprises of the same winding having with a small magnetic coupling between the coils. In an alternative embodiment, two or more solenoid coils having different inductances may be used. Since coils 730 are wound in transverse planes, the produced RF field is similar to the RF field produced by a solenoid. To this end, coils 730 are preferably substantially similar and carry similar currents.

Antenna 500 is preferably suitable for azimuthally symmetric and azimuthally focused NMR detection. In transmit mode, azimuthally uniform excitation of the formation is desired. Accordingly, all coils 730 may transmit in parallel. As a result, coils 730 generate an RF equivalent magnetic dipole centered at the origin and directed along the longitudinal axis of the tool. Since the axially-oriented $B_1$ field lines are substantially orthogonal to the radially-oriented static magnetic field $B_0$ in all azimuthal directions, NMR is induced in the entire sensitive volume. During reception of NMR echo signals, the signals from all coils are detected, amplified, and processed separately. A typical pulse sequence would be based on the CPMG sequence; a specific pulse sequence is described below.

Due to the sectional design of the antenna, the echo signals received by each coil correspond to subtending sectors of the sensitive volume. Certain azimuthal overlapping of the sensitive volume sectors may exist and should be considered during data processing and log interpretation. Radial extensions of the RF screens within recess regions 720 between the adjacent coils 730 allow some control over how much adjacent sectors overlap. By increasing the number core sectors 725, it is possible to achieve a fine azimuthal resolution on the NMR sensor.

Antenna Sleeve

In a preferred embodiment, antenna assembly 240 (or 700) is enclosed in a sleeve 270. An example construction of antenna sleeve 270 is described, for example, in U.S. Pat. No. 6,008,646, which is incorporated herein by reference. In particular, sleeve 270 is suitable to protect antenna assembly 240 against abrasions from particles in the drilling mud and impact against the earth formation. In a preferred embodiment, sleeve 270 is composed of a non-conductive, impact and wear resistant material, such as fiberglass or transition toughened zirconia. In an alternative embodiment, sleeve 270 may be composed of steel. In this embodiment, sleeve 270 should preferably have vertical slots cut therein at the top and the bottom of the antenna 260 to allow flux of magnetic field $B_1$ to enter and exit the magnetic assembly.

It should be noted that shield 270 may be extended to cover the entire magnetic assembly 200.

Alternative Antenna Assembly Embodiment(s)

Figure 9:
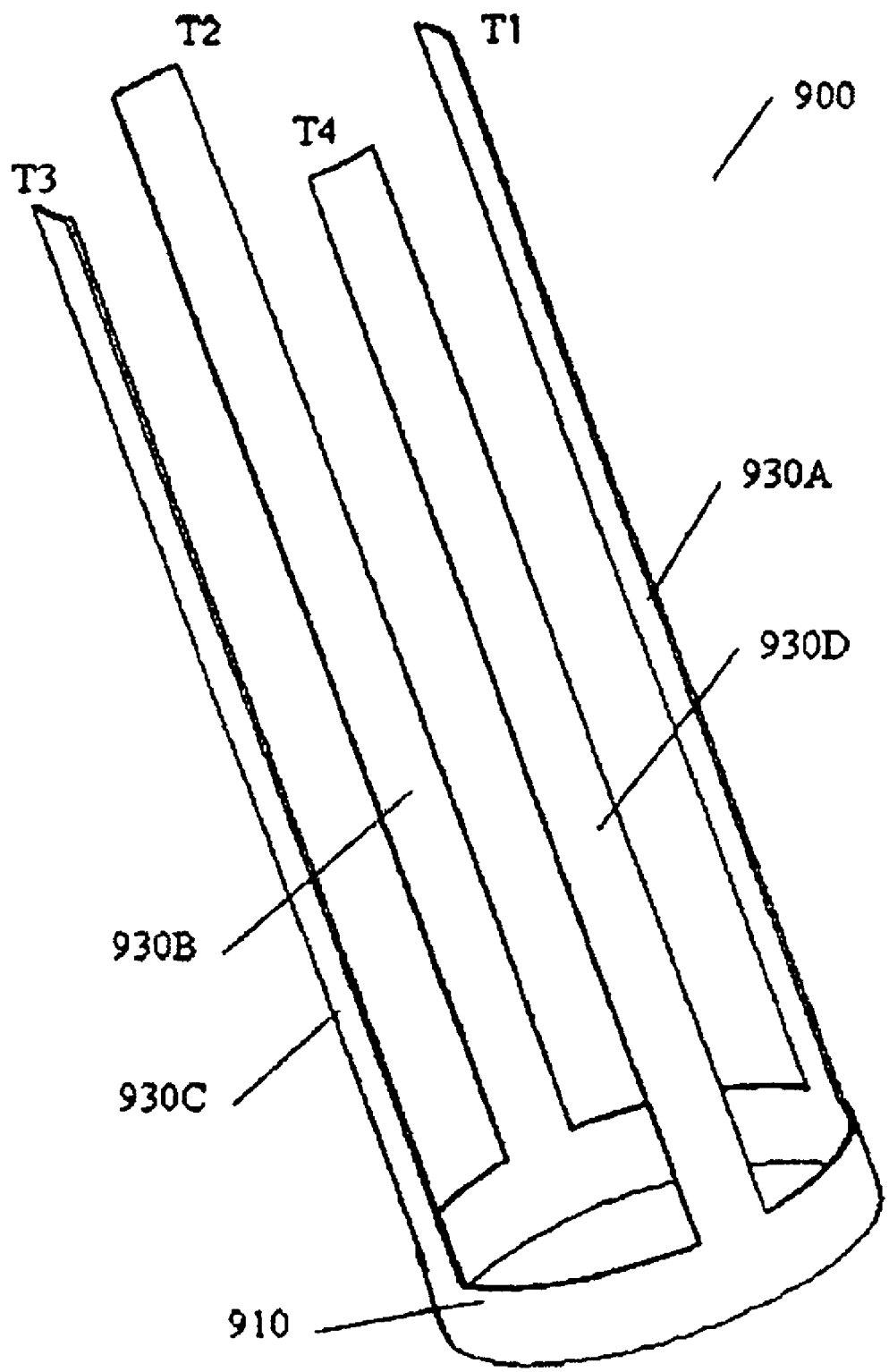
FIG. 9 illustrates a schematic cross-sectional view of an antenna according to another embodiment.

FIG. 9 illustrates another embodiment of an antenna assembly in accordance with the principles disclosed herein, with four longitudinal segments (strips) interconnected at one of their end. The use of this strips' arrangement allows NMR investigation of four quadrants about an axis of the logging tool. In particular, it is useful for determining directional properties of the surrounding formation with the aid of signals received at two or more, preferably adjacent antenna strips.

As shown in FIG. 9, antenna assembly 900 comprises four longitudinal strips 930A, 930B, 930C, and 930D spaced apart by 90 degrees and interconnected by means of an end ring 910. On the opposite end of the strips, four antenna terminals are located (T1, T2, T3, and T4). In accordance with a specific embodiment, antenna assembly 900 can include an antenna core placed inside the strips.

The four terminals (T1, T2, T3, and T4) of the antenna 900 can be connected to transmitter in eight different fashions: T1+T2, T2+T3, T3+T4, T4+T1, T1+T3, T2+T4, T1&T2+T3&T4, and T1&T4+T2&T3. In addition, the terminals of the antenna 900 that are not currently connected to transmitter can be shunted. The RF field produced by antenna 900 is similar to that of a saddle shaped antenna. For example, in order to get an RF field pattern shown in FIG. 3D, the T1&T2+T3&T4 strips combination should be connected to transmitter (T1&T2 means that two antenna terminals, T1 and T2, are shunted and connected to first transmitter terminal, while T3&T4 means that another two antenna terminals, T3 and T4, are also shunted and connected to second transmitter terminal).

Figure 10:
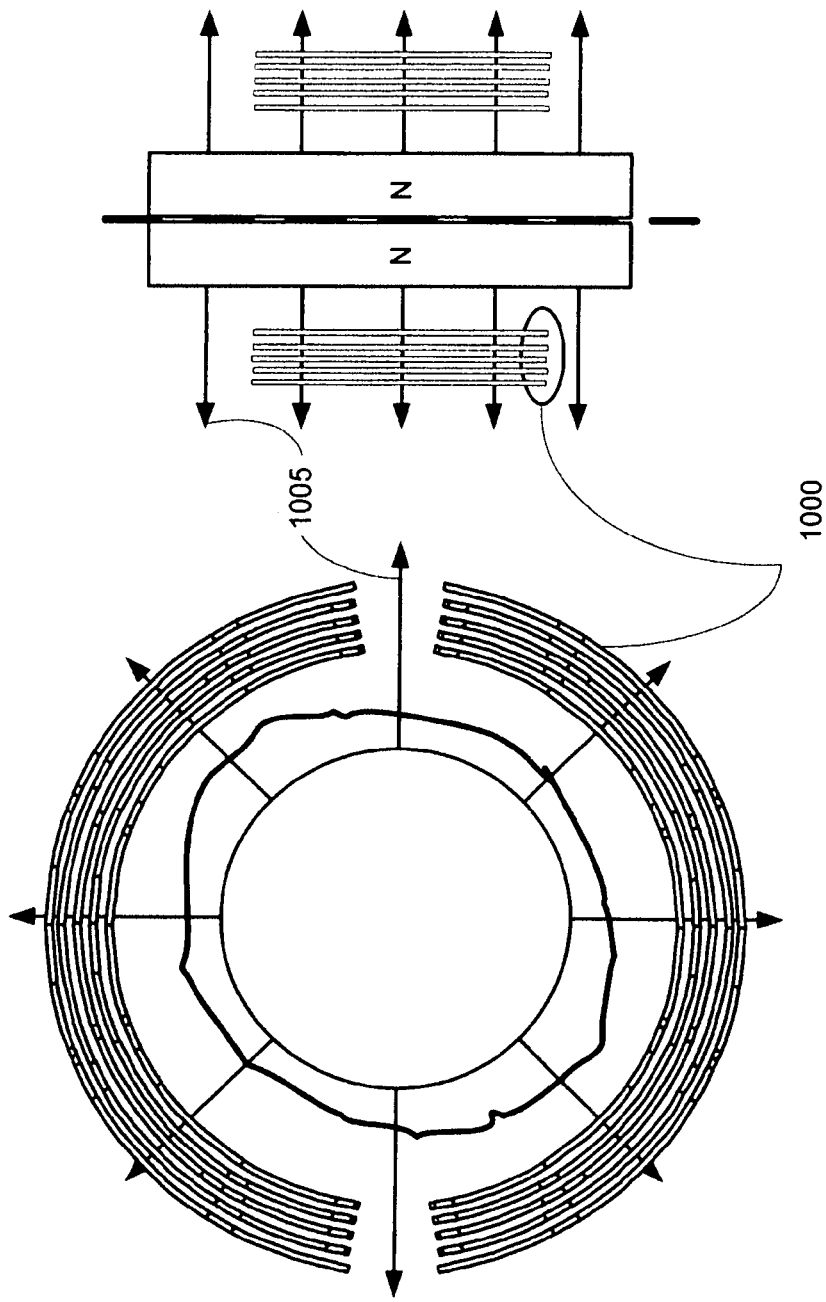
FIG. 10 illustrates the relative placement of sensitive volumes and a simulated monopole magnetic field.

This antenna design further breaks down the typically concentric sensitive volumes into four azimuthally-distinguishable quadrants. This antenna enables operation in large (12¼ in. and up) and potentially badly washed-out boreholes. This design also exploits the simulated-monopole static magnetic field discussed above. As noted, the magnetic monopole is simulated by the radially directed static magnetic field capable of reaching deep into the formation. In a preferred embodiment, a magnetic monopole is simulated by a logging tool having a substantially radial static magnetic field extending beyond about 60 cm into a formation surrounding the logging tool. FIG. 10 illustrates the relative location of sensitive volumes 1000 in a simulated monopole magnetic field represented by static magnetic field lines 1005.

In a preferred embodiment, radial separation between sensitive volumes is achieved by switching operating frequencies to selectively excite resonance at different radii. In a preferred embodiment, deploying the example antenna configuration disclosed herein, there are five (5) radial depths possible and four (4) azimuthal positions for a total of twenty (20) distinct sensitive volumes that may be addressed by the antenna.

In particular, there are two omnidirectional modes (N-S and E-W) and four directional modes (N, S, E and W). Notably, in a preferred embodiment individual quadrants are not being addressed; instead, two adjacent or all four quadrants resonate simultaneously. The signals from each measurement are, typically, not independent of each other. Decomposition into independent quadrant readings requires some additional steps, which are outlined below.

The change in magnet configuration requires some adjustments in field strength, operating frequencies and magnetic field gradient. For comparison, Table 1 below lists some of the operating parameters for the familiar omnidirectional frequency hopping designs.

TABLE 1

| Sensitive Volume Position | Radial Position (in) | Frequency (kHz) | Gradient (gauss/cm) |
| --- | --- | --- | --- |
| Innermost | 7.8 | 750 | 17.0 |
| Middle | 8.2 | 680 | 14.7 |
| Outer | 8.7 | 600 | 12.3 |

TABLE 2

| Sensitive Volume Position | Radial Position (in) | Frequency (kHz) | Gradient (gauss/cm) |
| --- | --- | --- | --- |
| Innermost | 6.0 | 500 | 8.0 |
| Middle | 6.5 | 450 | 6.6 |
| Outer | 7.5 | 400 | 5.3 |

Table 2 above lists comparable values for the directional design. As is readily seen, the frequencies have dropped by 200-250 kHz, and the gradient values are roughly cut in half. Therefore, all calculations that either explicitly calculate diffusivity values or otherwise rely on diffusion contrast to differentiate between fluid types are modified to take into account this change. Alternatively, the reduced magnetic field gradient can be compensated for by an increase in echo-to-echo spacing ($T_e$). The ratio of new echo spacing for the directional tool to that for omnidirectional familiar near borehole investigating tools should equal the ratio of new (and lower) field gradient to the old field gradients.

Figure 12:
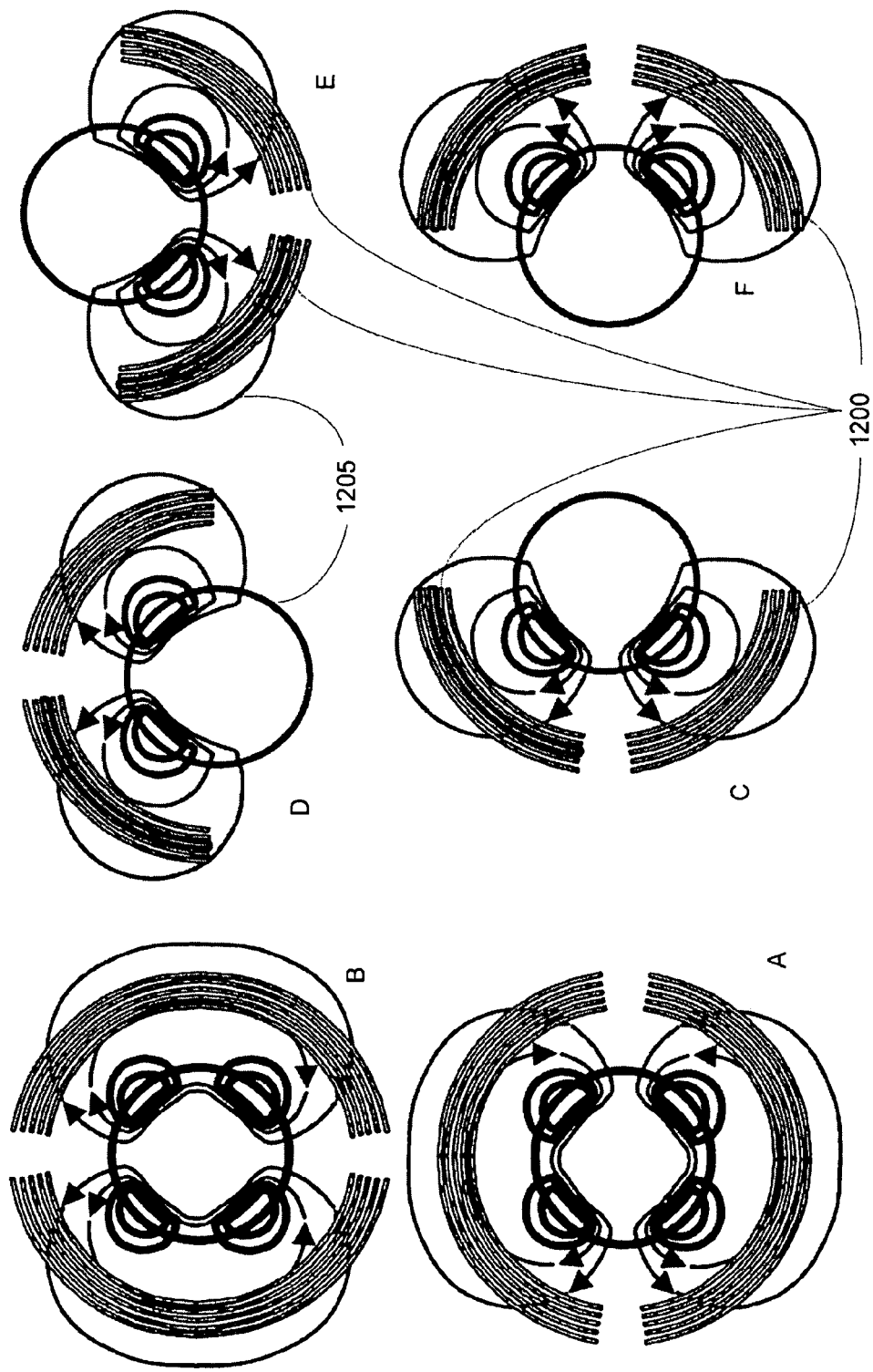
FIG. 12 illustrates six possible modes in one embodiment directed to obtaining directional resonance data.

The azimuthal sensitivity for the example directional antenna, however, has been reduced from 360° for the omnidirectional tool to less than 180°. In an example embodiment, the directional tool typically acquires data in 10 different volumes, staggered in 5 different depths of investigation (DOI). DOI ranges from 2.5 in. to 4 in. FIG. 12 illustrates six modes A-F of operation for the directional antenna having four longitudinal strips (FIG. 9). Also shown in FIG. 12 are sensitive volumes 1200 for each of the modes A-F. Each of the sensitive volumes corresponds to a different frequency NMR signal. However, it should be noted that although a plurality of sensitive volumes are depicted in the illustrative figures, this is not intended to be a limitation on the scope of the attached claims unless so indicated expressly. Also shown in FIG. 12, although not marked as such is a schematic antenna core in cross-section. These six modes are further described in Table 3 below:

TABLE 3

| Antenna Mode | Terminals used for transmitter connection | Signal Comes from Quadrants . . . |
| --- | --- | --- |
| Omni | T1&T2 + T3&T4 | All (represented by A in FIG. 12) |
| North (N) | T1 + T2 | NW and NE (represented by D in FIG. 12) |
| South (S) | T3 + T4 | SE and SW (represented by E in FIG. 12) |
| Omni | T4&T1 + T2&T3 | All (represented by B in FIG. 12) |
| East (E) | T1&T4 | NE and SE (represented by F in FIG. 12) |
| West (W) | T2&T3 | SW and NW (represented by C in FIG. 12) |

Figure 11:
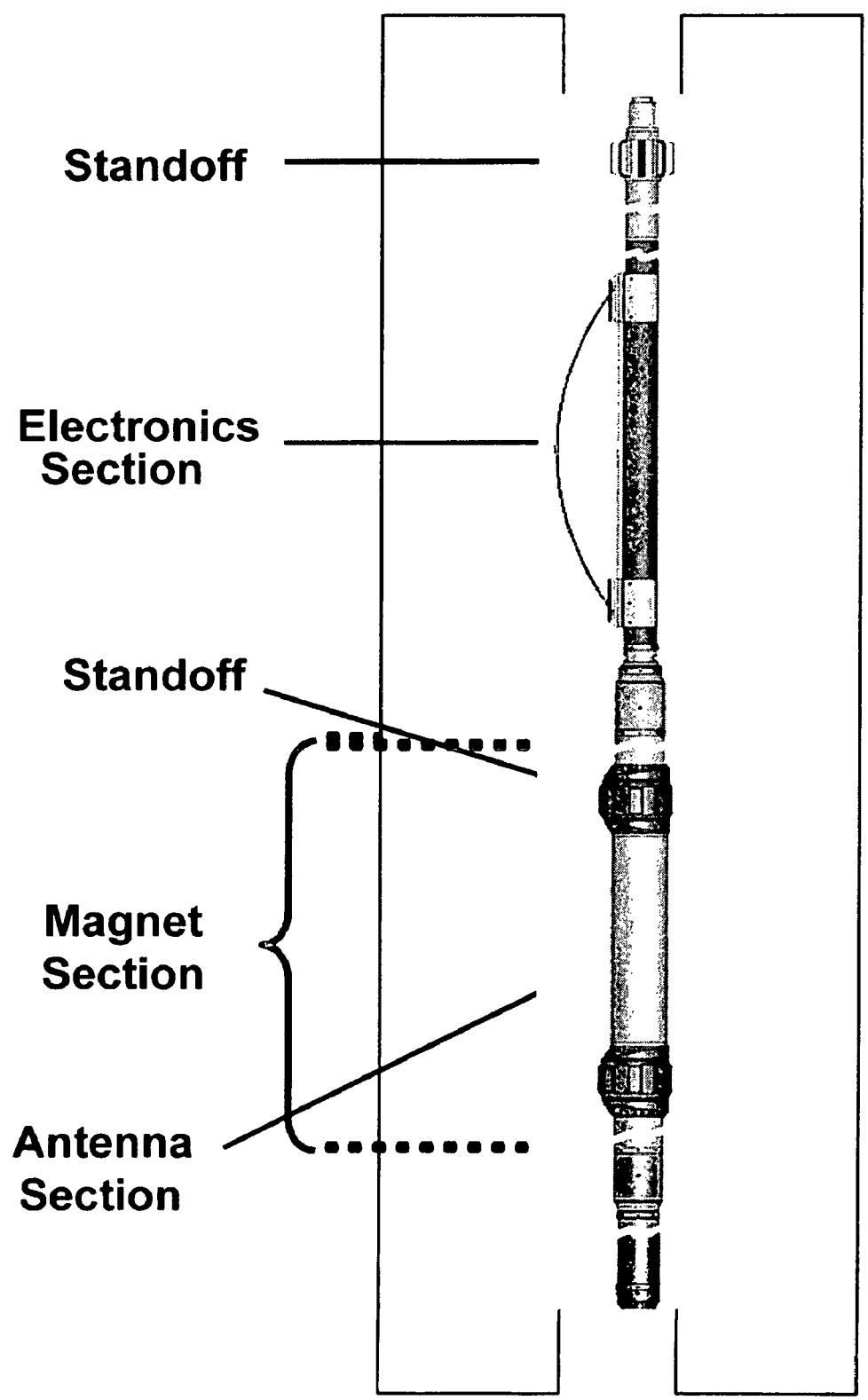
FIG. 11 schematically illustrates an example MRIL wireline tool (not to scale) placed against a borehole wall with standoffs and a bowspring.
Figure 16:
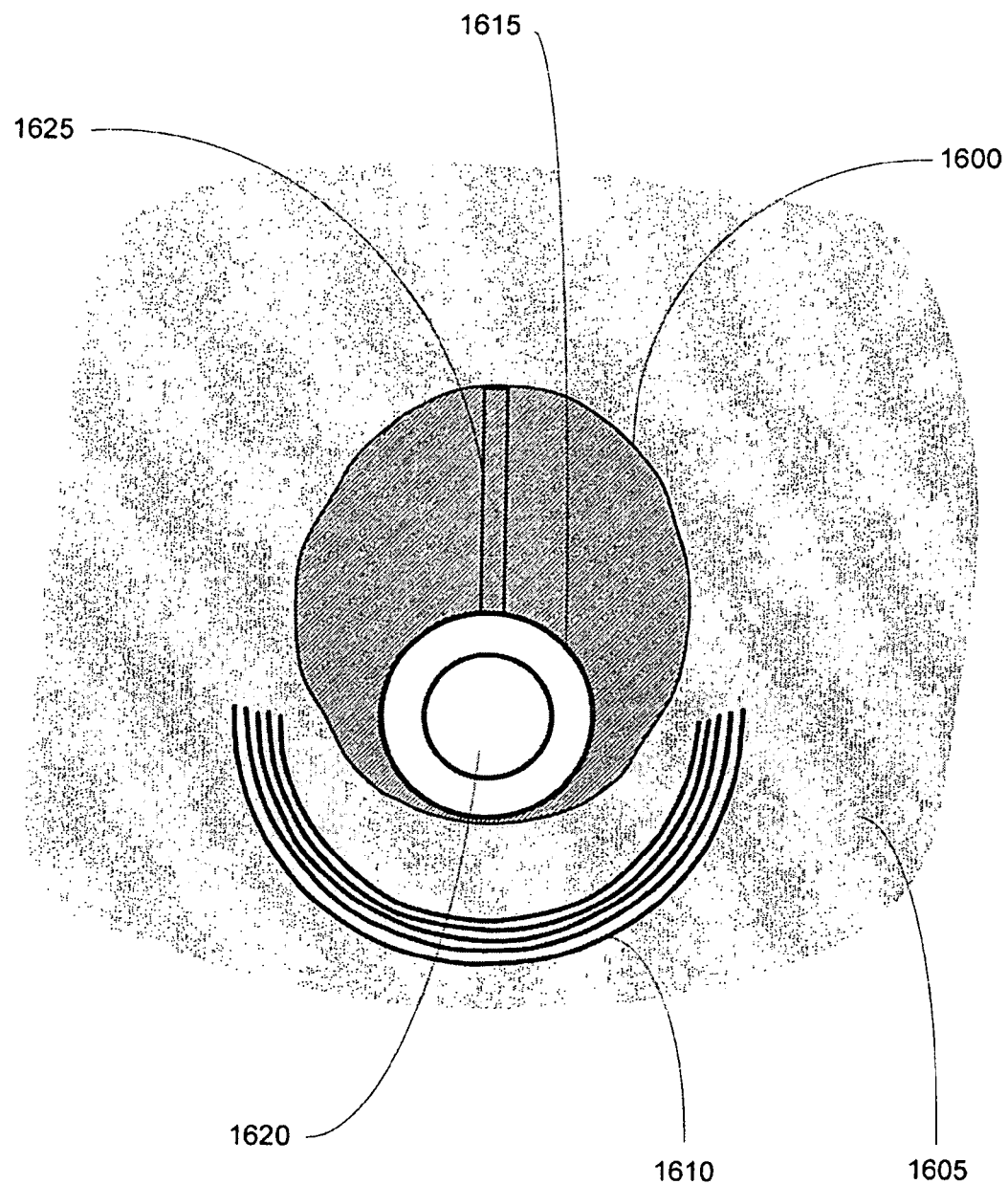
FIG. 16 shows a cross section of a logging tool close to a side of a borehole and corresponds to the illustration in FIG. 11.

In addition, there is no requirement that the directional tool be placed in the center of the borehole. Indeed, in a preferred embodiment, it is operated next to the borehole wall with asymmetric standoffs to provide a separation between the wall and the tool and bowsprings to keep in place, as illustrated in FIGS. 11 and 16. FIG. 16 shows a cross-sectional view of borehole 1600 in formation 1605 with sensitive volumes 1610 in the formation. Also shown are logging tool 1615 with central channel/cavity 1620 and bowspring 1625. FIG. 11 provides a side illustration of the tool. Thus, logging tool 1615 can collect data in washed out and asymmetric boreholes with relative ease due to the ease of fixing its position in asymmetric and irregular washed out boreholes.

The Downhole Electronics

Figure 1:
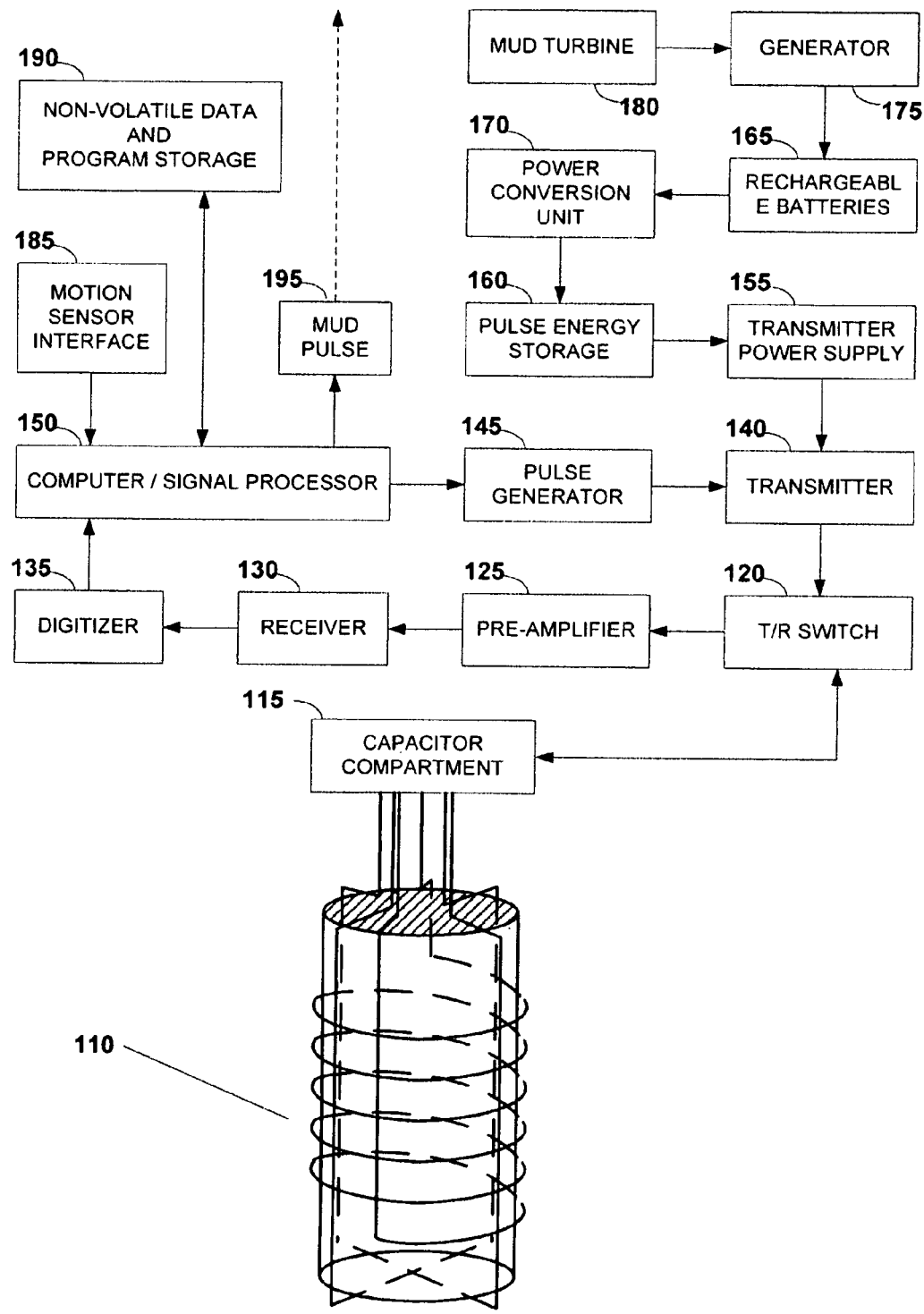
FIG. 1 is block/schematic diagram of electrical components of a NMR tool in accordance with a one embodiment.

FIG. 1 illustrates in a block-diagram form the preferred electronics arrangement for the NMR tool. In particular, transceiver RF antenna 110 is coupled to tuning capacitors (not shown) housed in a compartment 115, which is interfaced to a transmit/receive switch 120. During transmission, T/R switch receives pulsed RF power from transmitter 140, which is gated by pulse generator 145. Pulse generator 145 is under control of computer/signal processor 150. Pulse generator 145 controls the timing and operation of transmitter 140, which is powered by power supply 155. During reception, T/R switch 120 routes the received NMR signals to preamplifier 125, which in turn drives the receiver 130. The received, amplified signal is digitized in digitizer 135 and fed into computer/signal processor 150.

In a preferred embodiment, tuning capacitors are housed in a compartment 115. Tuning capacitors are preferably used to match the impedance of transceiver antenna 110 so that it will resonate at the desired natural frequency. As described, for example, in U.S. Pat. No. 5,557,201, compartment 115 is sealed off from the borehole environment, so that the capacitors remain at atmospheric pressure instead of being exposed to the high borehole pressures. This pressure-sealed design eliminates the need for filling the compartment 115 with oil, as in prior art, to prevent the capacitors from contacting borehole fluids. Additionally, a high-pressure antenna feed-through connector (not shown) is provided to establish a conductive path for the electrical current from transceiver antenna 110 to the tuning capacitors.

Figure 6:
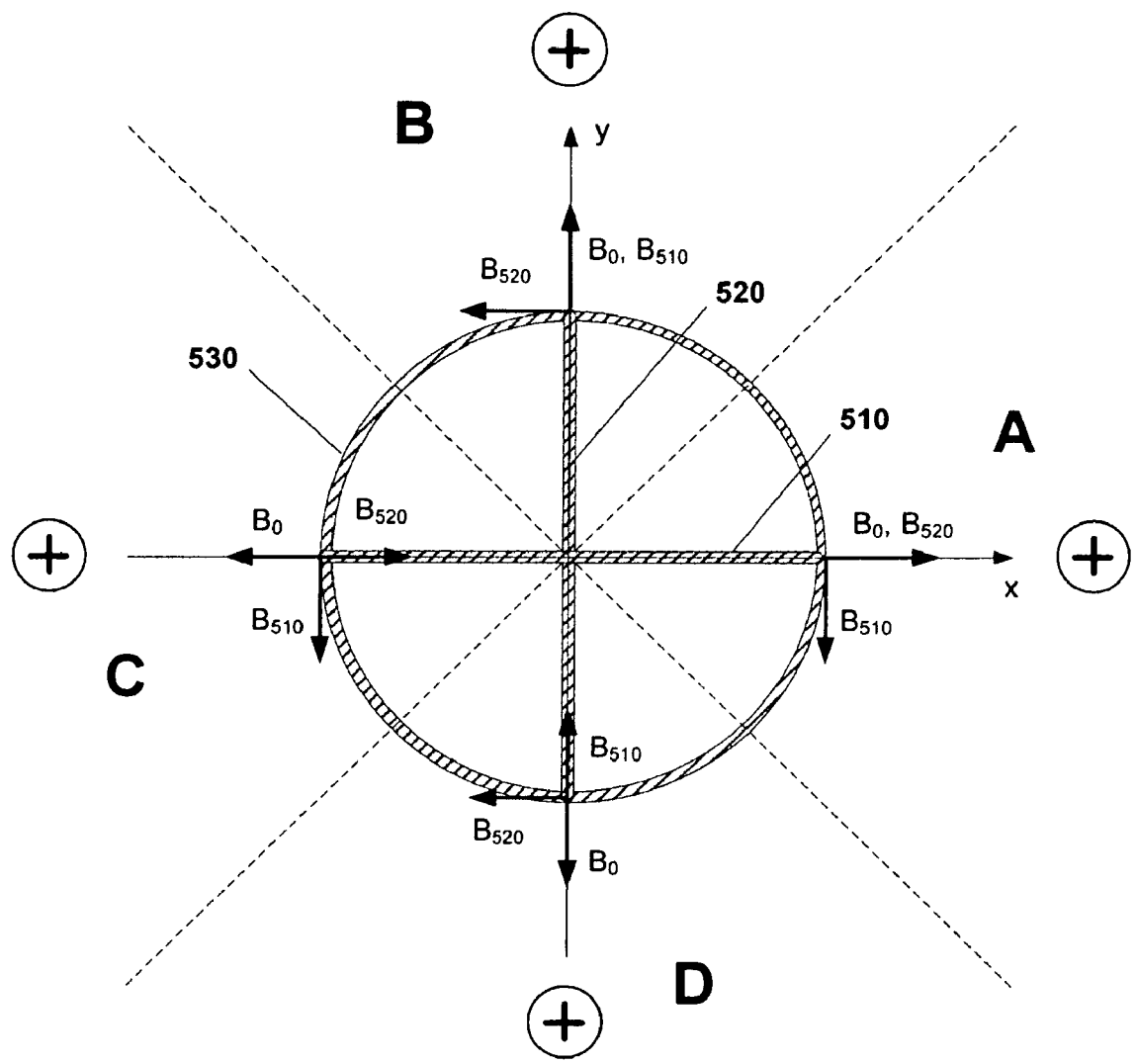
FIG. 6 is top view of a transceiver antenna in a preferred embodiment, with direction of magnetic fields indicated.

These inventors have found that by maintaining compartment 115 at atmospheric pressure, more pressure-sensitive electronics may be mounted inside compartment 115. This includes, but is not limited to, electromechanical relays and associated driver electronics. Under control of the driver electronics, such relays can be used to add more tuning capacitors to the resonant circuit formed by the fixed capacitors and the antenna. Thereby, the resonant frequency of the resonant circuit can be changed and the system can be made to operate at different frequencies one at a time. Such an arrangement is advantageous because by changing the operating frequency, a different sensitive volume is selected. By using multiple volumes one at a time, more signals can be accumulated in less time and/or different NMR measurements can be performed in a quasi-simultaneous fashion. Reference is made here to the paper "Lithology-Independent Gas Detection by Gradient NMR Logging," by Prammer, Mardon, Coates and Miller, Society of Petroleum Engineers, paper SPE-30562, published in the transactions to the 1995 SPE Annual Technical Conference & Exhibition, pp. 325-336, which is hereby incorporated by reference. In FIG. 6 of this paper, a pulse sequence for an NMR wireline tool is shown that utilizes two measurement volumes at once to affect oil and gas detection.

In a preferred embodiment, processor 150 receives real-time motion data from the motion sensor interface 185, which conditions the electrical signal from a plurality of motion sensors (not shown). The operation of the motion sensors is described in more detail in U.S. Pat. No. 6,362,619, which is incorporated herein by reference. Additionally, the processor reads from and writes to a non-volatile data and program memory 190. In a preferred embodiment, non-volatile memory 190 retains data even when the electronics is not supplied with electrical power. In a preferred implementation, non-volatile memory 190 uses "Flash" EEPROM integrated circuits. Another suitable option is a battery-powered low-power CMOS static RAM. Non-volatile memory 190 holds all data acquired during a run. Processor 150 performs real-time processing on the data to extract an indication of formation porosity and of log quality.

In a preferred embodiment, this data is converted into a data stream of preferably low bit rate and are fed into a mud-pulse system 195 that broadcasts the data stream to the surface by means of pressure pulses within the fluid column within the drill collar. Above-surface processing equipment (not shown) can be used to display the results to an operator. It will be appreciated that different tool-to-surface communication approaches are possible in alternative embodiments. Further, those skilled in the art will appreciate that downhole processor 150 may be implemented using two or more dedicated signal processors communicating with each other. In this embodiment, each processor can be performing a different task. For example, a dedicated processor can be used to measure the orientation of the tool with respect to earth coordinates (inclination from static acceleration and strike from the magnetic north direction), compute necessary parameters for directional drilling system, and process signals from various antenna elements to enable directional sensitivity. It is applicants' intention that any suitable processor configuration can be used in accordance with the principles described in this disclosure. Further, it should be apparent that various options that exist for storage of the acquired information and its communication to a user can be used in different practical embodiments.

FIG. 1 also illustrates the power generation in a block diagram form. In particular, as shown this power could be derived from one or more of the following sources: (1) from a turbine/generator combination 175 and 180 that converts a portion of the mechanical energy delivered by the flowing mud column into electrical energy, or (2) an (optional) bank of primary battery cells (not shown), typically of the lithium type. The generator can be used to directly drive the power conversion unit 170. A potential disadvantage of this arrangement is that the tool cannot operate without mud being continuously pumped from the surface through the drill collar through the NMR tool to the drill bit. This requirement could potentially interfere with the requirements of the drilling operation. Therefore, in a preferred embodiment, the turbine/generator combination is used to charge a bank of rechargeable secondary battery cells 165, for example of the nickel-cadmium or silver-oxygen type. In a preferred embodiment, the generator 175 is sufficiently powerful to recharge the secondary elements in a short amount of time, while these secondary cells supply electric power to the tool during the time when no or very slow mud flow exists.

Depth of Investigation

In accordance with a preferred embodiment, NMR measurements can be taken in shallow and deep volumes. As indicated above, measurements in deep sensitive volumes are primarily enabled by a strong static magnetic field $B_0$ having low field gradient $G_0$. As shown in FIG. 3E, magnetic field $B_0$ decreases as the distance from the tool increases. For example, 20 cm from the tool's axis the magnetic field $B_0$ is about 62 G; 80 cm from the tool's axis $B_0$ falls to about 14 G. The frequency at which the nuclear spins precess about the static magnetic field $B_0$ is directly proportional to the strength of static magnetic field $B_0$. This frequency is known as the Larmor frequency and is defined as $f=\gamma B_0/2\pi$. Thus, for an NMR tool to sense a particular distance into the formation, the frequency of the oscillating field $B_1$ is selected to match the Larmor frequency of the protons at that distance. In particular, a narrow frequency band is typically chosen, so that the sensitive volume is a thin cylindrical shell co-axial with the tool and surrounding the borehole.

To this end, the NMR system in accordance with a preferred embodiment conducts measurements in at least two sensitive volumes. Preferably, such sensitive volumes differ in 20 cm and 30 cm boreholes. In particular, if a 22-26 cm drill bit is used to drill a borehole, the preferred sensitive volumes are identified in Table 4 below:

TABLE 4

| | (≈20 cm borehole) | | | |
|---|---|---|---|---|
| | R | F | $B_0$ | $G_0$ |
| Shallow volume | 20 cm | 333 kHz | 78 G | 4.0 G/cm |
| Deep volume | 80 cm | 60 kHz | 14 G | 0.3 G/cm |

If a 26-32 cm drill bit is used to drill a borehole, the preferred sensitive volumes are identified in Table 5 below:

TABLE 5

| | (≈30 cm borehole) | | | |
|---|---|---|---|---|
| | R | f | $B_0$ | $G_0$ |
| Shallow volume | 30 cm | 200 kHz | 47 G | 1.4 G/cm |
| Deep volume | 80 cm | 60 kHz | 14 G | 0.3 G/cm |

Shallow and deep measurements in general serve different purposes. In particular, shallow volumes (i.e., 20 cm for smaller boreholes and 30 cm for larger boreholes) characterize flushed conditions. In a preferred embodiment, these volumes are used to replicate the conventional NMR logging measurements, such as porosity, $T_1$ and $T_2$ relaxation measurements, bound fluid volume, etc. These measurements characterize the pore space, the type and volume of bound fluids and volume available for producible (movable) fluids. Moreover, these shallow volumes can be used for invasion profiling. The deep measurements (i.e., 80 cm deep) enable hydrocarbon quantification in the deep regions that are free of borehole fluids. These deep readings, in a preferred embodiment, can be used to supplement the shallow free-fluid measurements by quantifying the amount of oil and gas present at a distance from the borehole. Thus, different combinations of at least one shallow and at least one deep measurement (and in other embodiments additional measurements at intermediate depths) enable a single magnet assembly built in accordance with the principles outlined above to provide a depth-model of the formation surrounding the borehole. In particular, it enables estimation of the borehole fluid invasion profile, along with standard porosity measurements predominantly obtained from shallow volume measurements, and producible hydrocarbon saturations, primarily obtainable from deep volume measurements. A significant advantage of the proposed single magnet assembly design is that all of these measurements can be obtained quisi-simultaneously, thus essentially obviating the need for separate logging runs, the possibility of depth mismatching, etc.

Directional NMR Detection

In accordance with a preferred embodiment, the NMR tool is capable of directional NMR detection. In particular, the directional sensitivity of the tool is provided by a RF transceiver antenna 500 and a novel data processing method. During transmission, the RF antenna imparts an azimuthally symmetric or azimuthally focused RF field $B_1$ within the zone of investigation. During NMR signal detection, the RF antenna 500 becomes azimuthally sensitive. The data processing method in a preferred embodiment enables analysis of the received NMR signals to determine which region of formation is characterized by a given NMR response. The directional sensitivity aspect of this application, in combination with conventional accelerometer and magnetometer readings, enables real-time payzone steering during borehole drilling.

FIG. 5 illustrates a three-coil RF transceiver antenna 500 in accordance with one embodiment. As described above, antenna 500 comprises two saddle coils 510 and 520, and a solenoid coil 530 wound around soft-magnetic core 550. With reference to FIG. 6, solenoid coil 530, when energized with AC current, produces oscillating field $B_1$ having vertical field lines (coming out of the paper plane), which are azimuthally orthogonal to the static magnetic field $B_0$. As a result, the entire sensitive volume is resonated. Subsequently, solenoid coil 530 is capable of detecting NMR signals from the entire resonance volume.

In contrast, saddle coils 510 and 520 are azimuthally sensitive. In particular, when saddle coils are energized with AC current, they produce oscillating field $B_1$ with magnetic field lines substantially orthogonal to the static magnetic field $B_0$ along their respective planes; in FIG. 6, for example, saddle coil 510 is capable of inducing NMR in regions along the x-axis, while saddle coil 520 is capable of inducing NMR in regions along the y-axis. The directions of $B_1$ magnetic field lines produced by coils 510 and 520 are indicated in FIG. 6 as $B_{510}$ and $B_{520}$, respectively. Subsequently, coils 510 and 520 may be used to detect NMR signals from the resonated sections of the sensitive volume. It should be noted that since the azimuthal sensitivity of a saddle coil antenna decreases as $\sqrt{\cos\phi}$, where $\phi$ is angular deviation from its plane, there is insignificant overlap between sensitive volumes of coils 510 and 520.

More specifically, antenna configuration 500 effectively divides the entire resonance volume of 360° into four measurement quadrants: A, B, C, and D, each covering sectors of approximately 90°. By alternately transmitting excitation pulses and receiving NMR signals between coils 510, 520, 530, a position of the hydrocarbon deposit can be narrowed down to one or more quadrants. In particular, solenoid coil 530 is suitable for detecting NMR signals from all four quadrants. Saddle coil 510 is suitable for detecting NMR signals from quadrants A and C, in which its magnetic field $B_{510}$ is substantially orthogonal to static field $B_0$. Saddle coil 520 is suitable for detecting NMR signals from quadrants B and D, in which its magnetic field $B_{520}$ is substantially orthogonal to static field $B_0$. It should be noted that since coils 510, 520, and 530 are independent, the NMR echoes can be received through the coils simultaneously.

In a preferred embodiment, all three coils may be used for transmission and reception resulting in nine possible measurements, shown in Table 6 below. (For clarity, in the remainder of this section coil 510 will be denoted as X, coil 520 will be denoted as Y, and coil 530 will be denoted as Z).

TABLE 6

| Tx | Rx | Volume Response | Comments |
|----|----|-----------------|----------|
| X | X | A + C | |
| X | Y | Overlap along diagonals | Not used |
| X | Z | A − C | Sign change due to mirror excitation |
| Y | X | Overlap along diagonals | Not Used |
| Y | Y | B + D | |
| Y | Z | B − D | Sign change due to mirror excitation |
| Z | X | A − C | Sign change due to mirror excitation |
| Z | Y | B − D | Sign change due to mirror excitation |
| Z | Z | A + B + C + D | Omnidirectional response |

From Table 6 it is observed that there are four types of measurements with different volume responses. The first type of response occurs when solenoid coil 530 is used both for transmission and reception (ZZ) resulting in an omnidirectional response. In this measurement, all four quadrants are resonated and NMR signals are also detected from all four quadrants (A+B+C+D). Such an omnidirectional response of solenoid coil 530 may be used as a reference for saddle coil measurements; in particular, it may correspond to a maximum 100% response in a water tank.

The second type of volume response occurs when: (1) the solenoid coil is used for transmission and either one of saddle coils is used for reception (ZX and ZY), or (2) either one of the saddle coils is used for transmission and solenoid coils is used for reception (XZ or YZ). In this measurement, a sign change takes place due to the relative orientation of $B_0$, $B_1$ (transmit, solenoid), and $B_1$ (receive, saddle coil). Accordingly, in a homogeneous medium, the spin signals would cancel out. In a heterogeneous medium, however, spin signals will indicate the presence of a difference between opposing quadrants.

The third type of volume response occurs when either one of the saddle coils is used both for transmission and reception, resulting in an azimuthally focused response. When coil 510 is used both for transmission and reception (XX), azimuthally focused sections along the x-axis are resonated: namely, quadrants A and C are resonated. Similarly, when coil 520 is used both for transmission and reception (YY), azimuthally focused sections along the y-axis are resonated: namely, quadrants B and D are resonated.

The fourth type of response occurs when one saddle coil is used for transmitting and the other is used for receiving (XY or YX). In this type of measurement, resonance volumes overlap along quadrant diagonals due to the orthogonality of saddle coils 510 and 520 and decrease in radial sensitivity of saddle coils with increase in angular deviation from its planes. As a result, the received NMR signal is weak and unsuitable for accurate measurement.

The first three volume responses may be used in accordance with a preferred embodiment to provide directional sensitivity. First, the excitation pulses are alternately transmitted through each antenna coil. Then, the NMR signals from all three coils are detected and amplified. Next, they are processed to generate five signal components (i.e., quadrant signatures) A, B, C, D, and the onmidirectional signal.

In one embodiment, the quadrant signatures may be computed by constructing and solving systems of linear equations from data provided in Table 6, as shown below.

$$\left.\begin{array}{l}XX = A + C \\ ZX = A - C\end{array}\right\} \to XX + ZX = 2A \to A = \frac{1}{2}(XX + ZX) \quad \text{Eq. 1}$$

$$\left.\begin{array}{l}YY = B + D \\ ZY = B - D\end{array}\right\} \to YY + ZY = 2B \to B = \frac{1}{2}(YY + ZY)$$

$$\left.\begin{array}{l}XX = A + C \\ ZX = A - C\end{array}\right\} \to XX - ZX = 2C \to C = \frac{1}{2}(XX - ZX)$$

$$\left.\begin{array}{l}YY = B + D \\ ZY = B - D\end{array}\right\} \to YY + ZY = 2D \to D = \frac{1}{2}(YY + ZY)$$

It should be noted that ZX measurement may be interchanged with XZ measurement, and YZ measurement with ZY measurement.

In another embodiment, quadrant signatures may by derived by forming and solving an over-determined matrix, as shown below.

$$\begin{bmatrix} XX \\ ZX \\ YY \\ ZY \\ ZZ \end{bmatrix} = \begin{bmatrix} 1 & 0 & 1 & 0 \\ 1 & 0 & -1 & 0 \\ 0 & 1 & 0 & 1 \\ 0 & 1 & 0 & -1 \\ 1 & 1 & 1 & 1 \end{bmatrix} * \begin{bmatrix} A \\ B \\ C \\ D \end{bmatrix} \quad \text{Eq. 2}$$

The solution to this matrix is given by the following pseudo-inverse matrix:

$$\begin{bmatrix} A \\ B \\ C \\ D \end{bmatrix} = \frac{1}{6}\begin{bmatrix} 2 & 3 & -1 & 0 & 1 \\ -1 & 0 & 2 & 3 & 1 \\ 2 & -3 & -1 & 0 & 1 \\ -1 & 0 & 2 & -3 & 1 \end{bmatrix} * \begin{bmatrix} XX \\ ZX \\ YY \\ ZY \\ ZZ \end{bmatrix} \quad \text{Eq. 3}$$

Eq. 4 below provides linear form of quadrant signatures given in matrix form in Eq. 3.

$A=\frac{1}{6}(2XX+3ZX-YY+ZZ)$ $B=\frac{1}{6}(-XX+2YY+3ZY+ZZ)$ $C=\frac{1}{6}(2XX-3ZX-YY+ZZ)$ $D=\frac{1}{6}(-XX+2YY-3ZY+ZZ)$   Eq. 4

After processing received NMR signals in manner shown above, five signal components A, B, C, D, and the omnidirectional response are available. Then, in a preferred embodiment, the directional signal components may be assigned to four quarter-cylinders located around the borehole by simultaneously measuring the orientation of the tool with respect to earth coordinates (inclination from static acceleration and strike from the magnetic north direction). In a vertical borehole, these quarter-cylinders cover the compass directions (i.e., North, South, East, and West). In a horizontal borehole they correspond to the directions above, below, left, and right. These tool orientation parameters are typically determined by accelerometers and magnetometers disposed within the tool string and measuring earth's gravitational vector compass directions, respectively.

An illustrative example of the above methods for directional NMR detection is provided next. Assume, for instance, that only quadrant A contains hydrocarbons. In such a case, the ZZ measurement will result in 25% response, as compared to 100% response of solenoid coil when hydrocarbons are present in all four quadrants. The XX measurement will result in 25% response, as compared to 100% response of solenoid coil, because saddle coil has about 50% sensitivity of solenoid coil Z. The YY measurement will result in approximately 0% response, because saddle coil Y is substantially insensitive in quadrants A and C. The ZX (or XZ) measurement will result in 25% response, for substantially similar reasons as ZZ and XX measurements. Finally, the ZY (or YZ) measurements will result in approximately 0% response, for the substantially similar reasons as YY measurements.

The following quadrant signatures are derived using the linear form given in Eq. 1:

$A=\frac{1}{2}(XX+ZX)=\frac{1}{2}(0.25+0.25)0.25$ $B=\frac{1}{2}(YY+ZY)=\frac{1}{2}(0+0)=0$ $C=\frac{1}{2}(XX-ZX)=\frac{1}{2}(0.25-0.25)=0$ $D=\frac{1}{2}(YY-ZY)=\frac{1}{2}(0-0)=0$ The results indicate that the entire signal is coming from quadrant A.

The same result is reached using the matrix form given in Eq. 4:

$A=\frac{1}{6}(2XX+3ZX-YY+ZZ)=\frac{1}{6}(0.5+0.75+0.25)=0.25;$ $B=\frac{1}{6}(-XX+2YY+3ZY+ZZ)=\frac{1}{6}(-0.25+0.25)=0;$ $C=\frac{1}{6}(2XX-3ZX-YY+ZZ)=\frac{1}{6}(0.5-0.75+0.25)=0;$ $D=\frac{1}{6}(-XX+2YY-3ZY+ZZ)=\frac{1}{6}(-0.25+0.25)=0.$ For the third antenna embodiment, Table 3 illustrates several modes of operation including four directional modes and two omnidirectional modes. For the directional modes it is preferable to account for interactions between antennas, reflected in two adjacent (or close together) antenna segments receiving NMR signals from more than one sensitive volume quadrant. As shown in FIG. 12, a directional antenna has six radiation patterns. In any of these modes, the NMR signal comes from either four or two quadrants in omnidirectional and in directional modes, respectively. For example, if the antenna radiates in North (N) direction, the signal comes from the north-easterly and north-westerly quadrants.

The system of all these possible measurements is redundant, because any measurement can be expressed as a linear combination of some others. Overall, there are only three linearly independent modes, which, at first, appears to be insufficient to derive individual, per-quadrant contributions. In a preferred solution of this linearly over- and underdetermined problem only the four directional modes are uses. In matrix notation, the relationship between measurements and quadrant contributions can be written down as follows:

$$\begin{bmatrix} N \\ E \\ S \\ W \end{bmatrix} = \begin{bmatrix} 1001 \\ 1100 \\ 0110 \\ 0011 \end{bmatrix} X \begin{bmatrix} NE \\ SE \\ SW \\ NW \end{bmatrix}$$

where the vector $[N\ E\ S\ W]^T$ represents acquired data and where $[NE\ SE\ SW\ NW]^T$ are the corresponding, unknown quantities for the individual quadrants. Because the mapping matrix presented above is singular and has no inverse, the linear system is not readily solvable. In a possible approach used in one embodiment, a solution may be obtained using computer tomography backprojection techniques. In one implementation, the individual sectors are approximated as:

$$\begin{bmatrix} NE \\ SE \\ SW \\ NW \end{bmatrix} = \frac{1}{2} \begin{bmatrix} 1100 \\ 0110 \\ 0011 \\ 1001 \end{bmatrix} X \begin{bmatrix} N \\ E \\ S \\ W \end{bmatrix}$$

In this solution, although robust, the information from any quadrant is "smeared" over the two adjacent ones as well. The method can be applied to raw echo data as well to the processed logging data.

In a preferred embodiment, it is possible to solve the underdetermined equation system under the additional constraint of non-negativity. In practice, the entire processing chain from NMR echoes to the log quantities, porosity, bound fluid volume, etc., is, preferably, carried out in the original NESW space. The backprojection is only performed at the level of log curves, which are all bound to be non-negative quantities. An interpretation of the quantities N, E, S, W and NE, SE, SW, NW is that they stand for log data quantities such as NMR porosity, bound fluid porosity, etc. At this level:

$$\begin{bmatrix} N \\ E \\ S \\ W \end{bmatrix} - \begin{bmatrix} 1001 \\ 1100 \\ 0110 \\ 0011 \end{bmatrix} X \begin{bmatrix} NE \\ SE \\ SW \\ NW \end{bmatrix} \rightarrow \min, \text{ for } \begin{bmatrix} N \\ E \\ S \\ W \end{bmatrix} \geq 0$$

Figure 13:
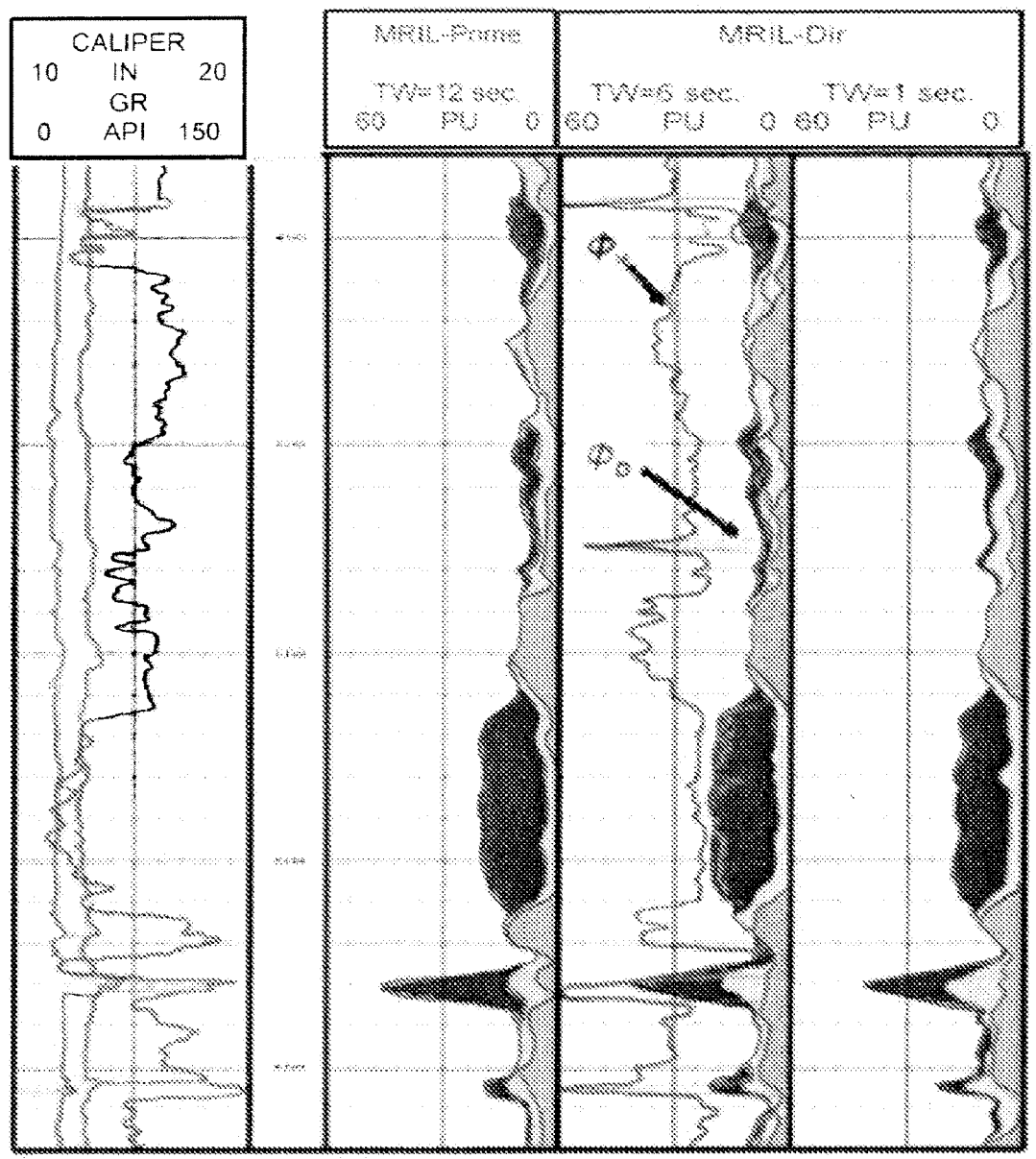
FIG. 13 provides comparison between data obtained with MRIL-Prime and directional MRIL tool embodiments.
Figure 14:
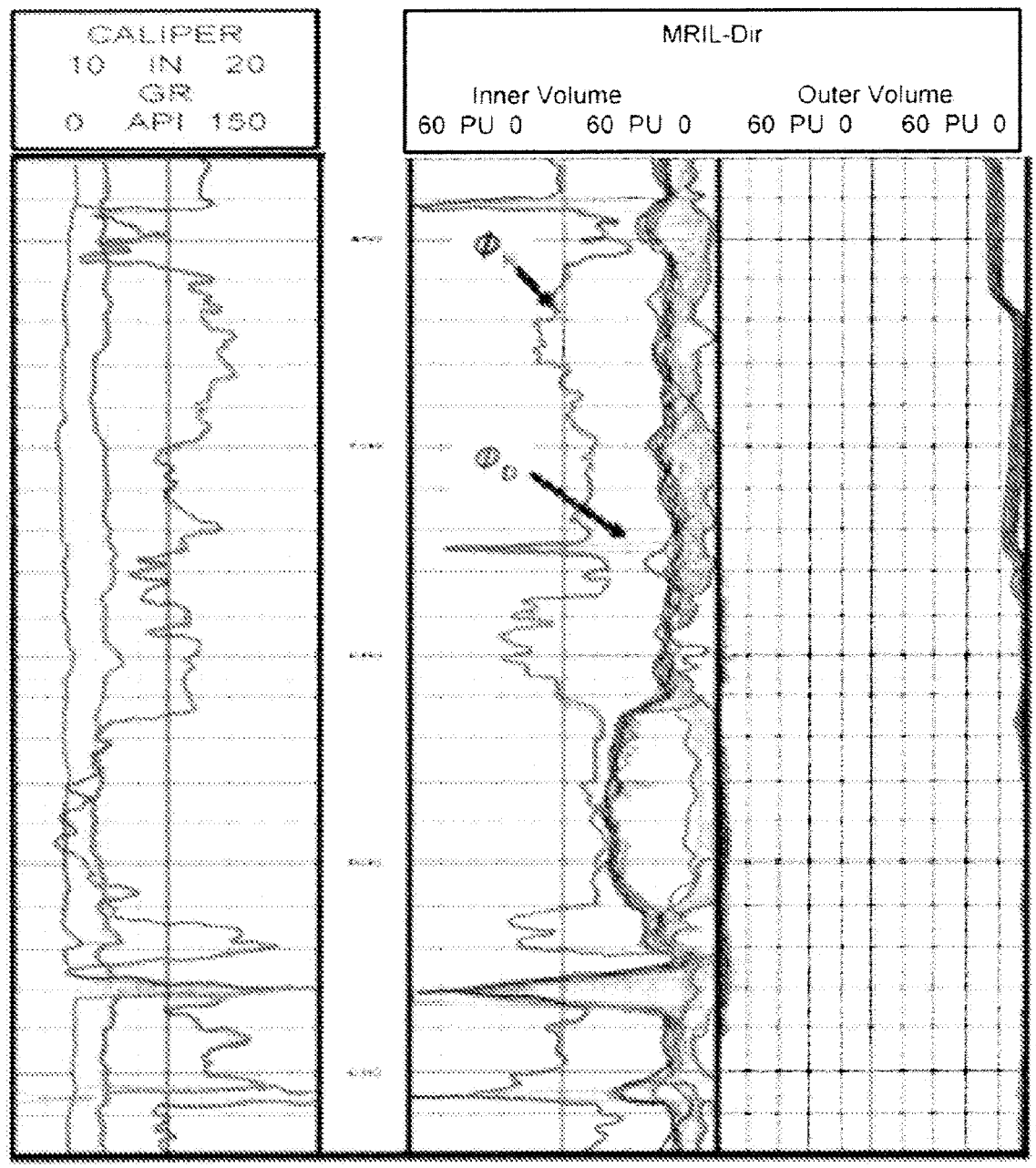
FIG. 14 illustrates results of the repeatability test comprising repeat logs of a well taken at different points in the borehole.
Figure 15:
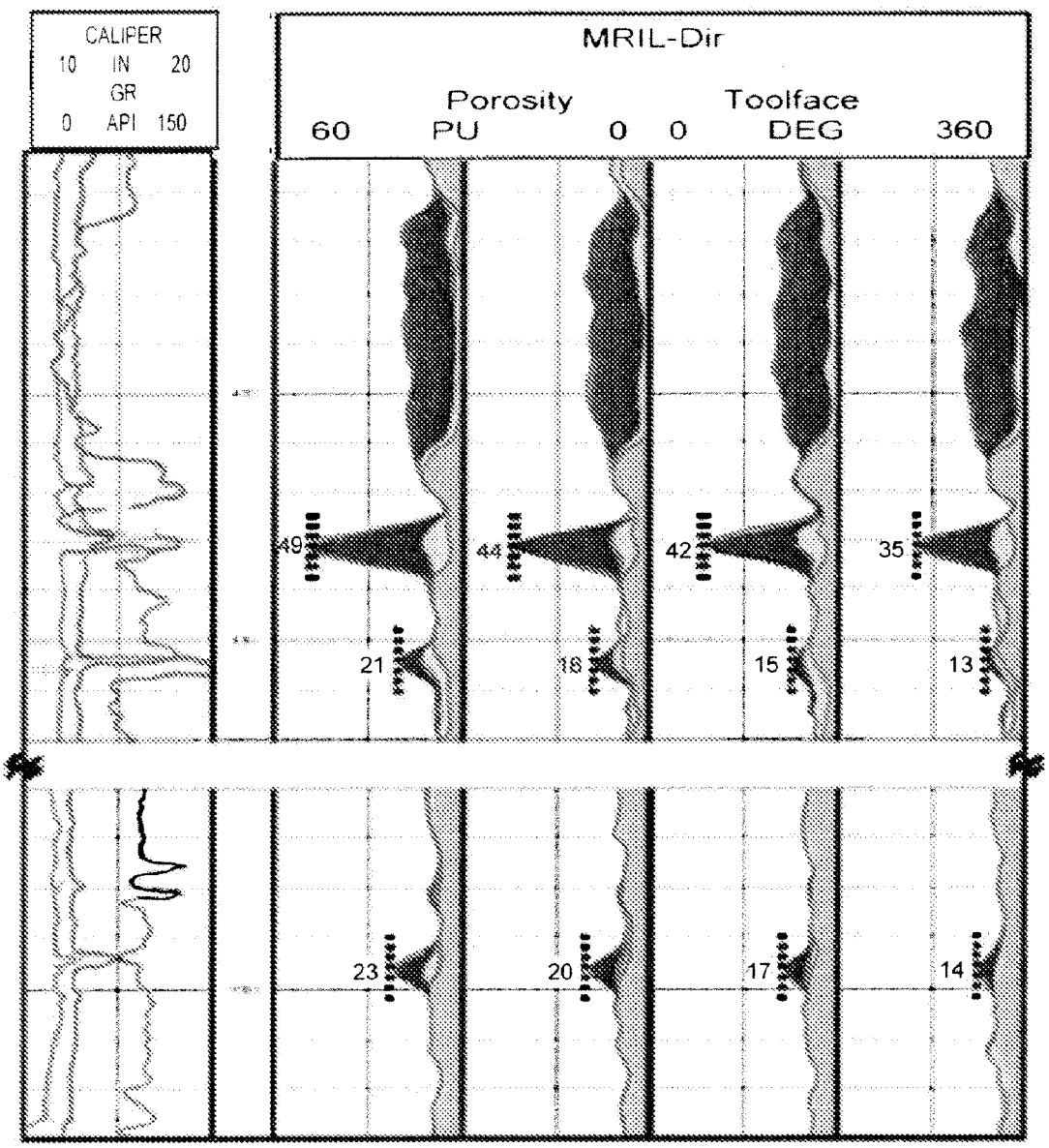
FIG. 15 shows data from different sensitive volumes of the directional tool.

This form of the problem is solvable with a number of commercial software packages, such as MATLAB. Some examples of directional data collected with an example antenna having a design as in FIG. 9 are shown in FIGS. 13-15. In FIG. 13, Track 1 displays the Gamma Ray log and the minimum and maximum diameters. Track 2 presents data acquired with Halliburton's MRIL Prime tool at a logging speed of 15 ft/min. Track 3 and 4 shows long (8 s) and short (1 s) wait time logs recorded with the directional antenna of FIG. 9. Track 3 also displays Neutron/Density porosity. The directional antenna logs were acquired at a logging speed of about 9 ft/min. The dark areas in tracks 2-4 denote free fluid, the light gray areas represent capillary bound fluid, and the intermediate gray areas stand for clay bound fluid.

This test shows that the directional antenna-based logging tool produces logs substantially similar to those of an omnidirectional logging tool. In this water well, the highest relaxation times are about 0.5 s. Therefore, the 1-s wait time is insufficient for full polarization in the sands, and the amplitudes appear slightly depressed compared to 8-s wait time data.

FIG. 14 shows the results from seven different runs in a repeatability test (both up- and down-logs). Track 3 shows the toolface orientation, where 0° (or 360°) indicates that the sensor is facing downwards. The results were nearly identical. In track 2 of FIG. 14, seven repeats of the upper section are shown. All results are in very good agreement. The standard deviation of total porosity is about 1 pu.

FIG. 15 shows illustrative data from different sensitive volumes, in particular the long-wait-time (8 s) data from four different sensitive volumes. These four volumes are used to acquire dual-wait-time data (1 s and 8 s) at an echo spacing of about 1.2 ms. The fifth volume is used for the high-precision claybound porosity measurement at echo spacing of about 0.6 ms. Data from the upper section and a lower section of the well are presented separately. Where the well is in fair condition, that is, where the well is round or elliptical without washouts, the NMR amplitudes from the four volumes agree with each other. In the event of washouts (at 630, 655 and 994 ft), however, the difference becomes obvious: the innermost volume contains a larger amount of borehole signal than the outermost volume. In this fresh water well, the borehole signal appears as free fluid. In the washouts, the inner volumes (tracks to the left) contain more borehole signal than the outer volumes (tracks to the right). The Depth of Investigations (DOIs) range from 2.8 in. to 4.0 in. The actual NMR amplitudes in the washouts are indicated by numbers. The pattern of monotonically decreasing amplitudes is characteristic of washouts and is useful for assessing whether or not the NMR porosity is affected by borehole signal. Actual drilling muds, however, have $T_2$ relaxation times fast enough to masquerade as bound fluids (less than 30 ms). In both cases, the stair-case pattern of reduced NMR amplitude with increased DOI is characteristic of washouts and a useful log quality indicator of directional MRIL data.

Figure 17:
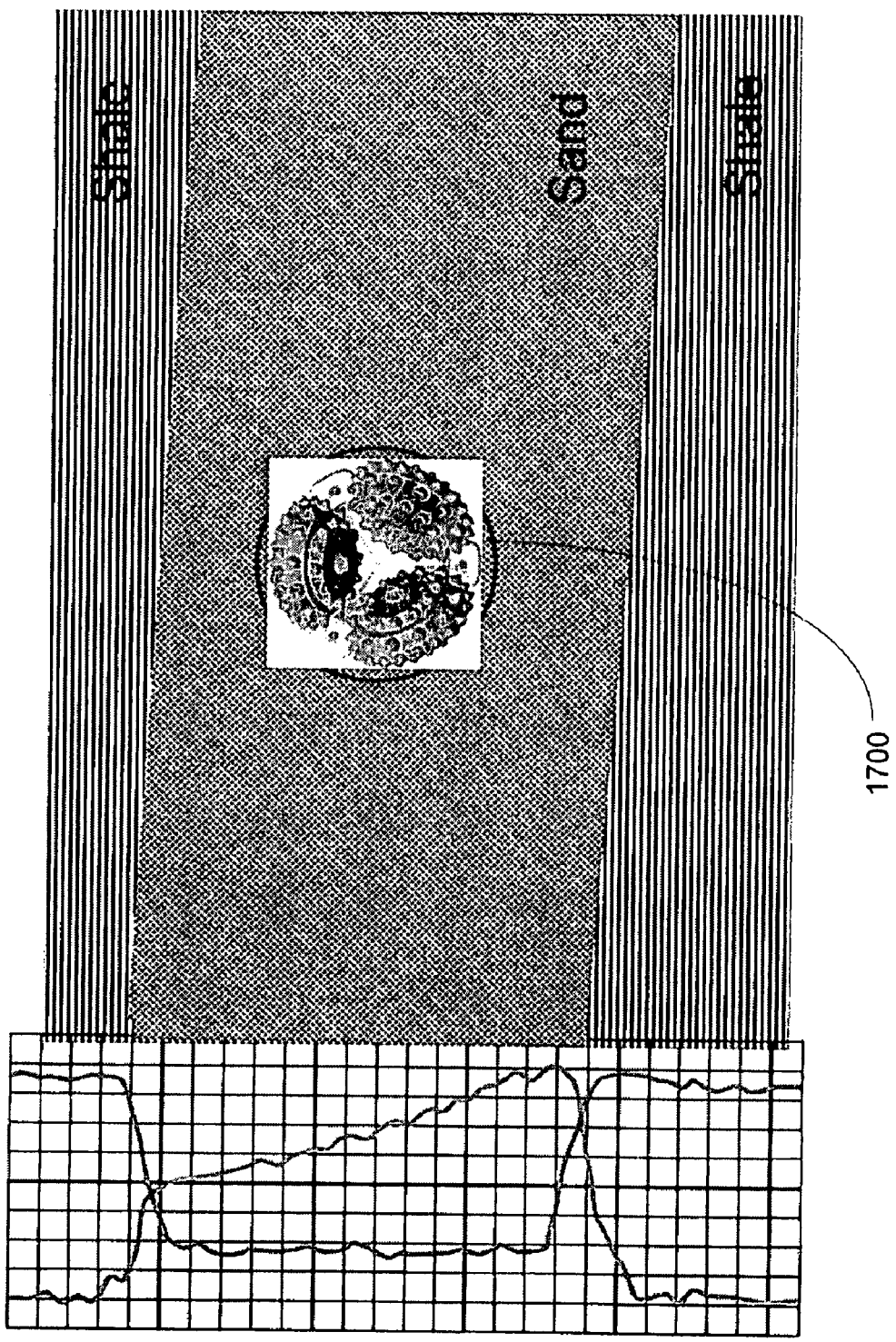
FIG. 17 illustrates directional drilling using a directional antenna configuration combined with the deep-looking capabilities in an exemplary embodiment.

As shown in illustrative FIG. 17, directional data is useful for determining a path for directing a drill into a formation region of interest. Shown in FIG. 17 is a sand layer interposed between a two shale deposits with a drill head 1700 traversing the sand layer. A corresponding set of signals is shown to indicate the directing of the drill head based on the acquired directional data including deep looking data that is required for effective directional drilling with the aid of NMR data.

As previously described, antenna configuration in FIGS. 5 and 9 effectively divides the entire resonance volume of 360° into four measurement quadrants: A, B, C, and D, each being approximately 90°. As an illustration, by alternately transmitting excitation pulses and receiving NMR signals between, for instance, coils 510, 520, 530, a position of the hydrocarbon deposit can be narrowed down to one or more quadrants. While solenoid coil 530 is suitable for detecting NMR signals from all four quadrants, saddle coil 510 primarily detects NMR signals from quadrants A and C and saddle coil 520 similarly detects NMR signals from quadrants B and D.

Thus, if a hydrocarbon deposit is present in quadrant A relative to the logging tool, then solenoid coil 530 and saddle coil 510 detect a relatively strong signal while saddle coil 520 typically fails to detect a signal from the deposit in quadrant A. In a preferred embodiment, all three coils may be used for transmission and reception resulting in nine possible measurements. Such information about the location of hydrocarbon deposits relative to the logging tool may be advantageously used in directional drilling to direct a drill towards quadrant A, including by using the antenna arrangement shown in FIG. 9. In a LWD tool, the directing of the drill can be accomplished using a feedback mechanism based on acquired NMR data, particularly deep NMR data that is most effective in reliably locating formation properties away from the potentially compromised neighborhood of the tool.

Pulse Sequences and Signal Processing

Figure 8:
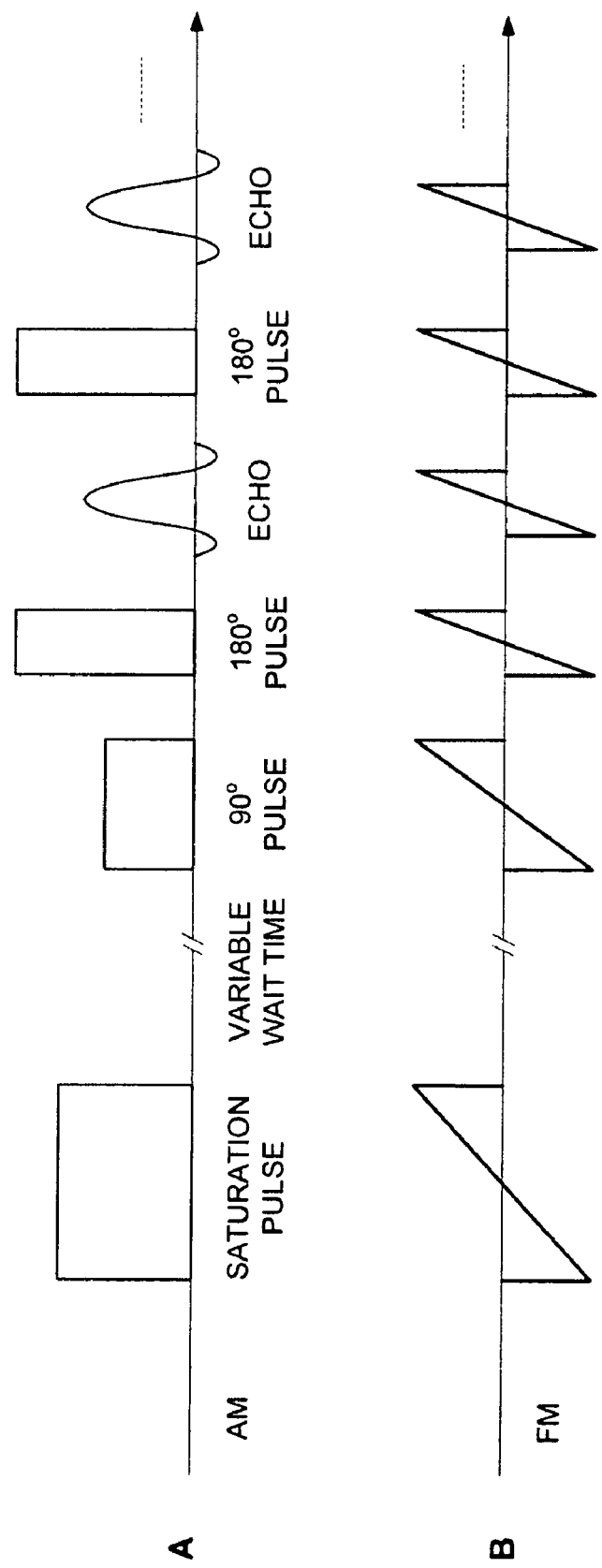
FIG. 8 illustrates a frequency-modulated CPMG pulse sequence used in one embodiment.

In accordance with a preferred embodiment, the NMR relaxation time measurements are determined using longitudinal relaxation times $T_1$. The $T_1$ pulse sequence is designed to improve signal-to-noise ratio of NMR signals from the deepest volumes of the formation. With reference to FIG. 8, the pulse sequence comprises at least one radio frequency pulse sweeping through a relatively wide range of frequencies to saturate the nuclear magnetization in a cylindrical volume around the tool; transmitting a frequency-swept readout pulse followed by a predetermined wait time; applying at least one frequency-swept refocusing pulse following the readout pulse; receiving at least one NMR echo corresponding to the readout pulse.

In a preferred embodiment, at the start of a measurement, one or more radio frequency pulse sweeping through a relatively wide range of frequencies is generated to saturate the nuclear magnetization in a cylindrical volume around the tool. In a preferred embodiment, the saturation pulse has bandwidth of about 10 kHz, duration of about 20 ms and sweeping rate of about 500 Hz/ms at full amplitude. Such saturation pulse generates $B_1$ magnetic field with gradient of about 0.3 G/cm in an annular region of about 6.5 cm wide. Of course, changing the range of RF frequencies varies the position and the width of the sensitive region in the formation.

Next, in accordance with a preferred embodiment, the saturation pulse is followed by a variable saturation recovery delay and a read-out pulse sequence. The readout pulse sequence preferably comprises a 90° pulse (i.e., excitation pulse) and a 180° pulse (i.e., refocusing pulse), followed by data acquisition window. The steps of applying a 180° pulse and data acquisition window are may be repeated. In a specific embodiment, the 90° pulse and 180° pulse are frequency-swept. More specifically, the 90° pulse is about 8 ms long, sweeping at 250 Hz/ms at ¼ of full amplitude. The 180° pulse is about 4 ms long, sweeping at 500 Hz/ms at full amplitude. Both pulses have bandwidth of about 2 kHz, which corresponds to an annulus of about 1.4 cm.

The above-described pulse sequence achieves the refocusing of the entire volume in a single spin echo. Therefore, the echo amplitude is about four times as strong as from a single-frequency sequence. The echo bandwidth, however, is doubled, resulting in a net SNR gain of 2.

The measurement process described above may be repeated for a series of increasing wait times as described, for example, in U.S. Pat. No. 6,051,973 and U.S. Pat. No. 6,242,913, both incorporated herein by reference. The wait times can, for example, be equally distributed on a logarithmic scale. In a specific embodiment, wait times are stepped through two or more of 1 ms, 3 ms, 10 ms, 30 ms, 100 ms, 300 ms, 1000 ms, 3000 ms and 6300 ms, and the measurement results are stacked to produce several data points on a multi-component $T_1$ relaxation curve. A data point corresponding to the longest wait time is obtained by a readout pulse sequence which is not preceded by a saturation pulse.

Finally, in accordance with a preferred embodiment, the produced $T_1$ relaxation curve is used to derive petrophysical properties of the formation, as known in the art. In particular, the resultant $T_1$ relaxation curve is processed to extract the dominant $T_1$ relaxation modes, from which amounts of bound water, free water and hydrocarbons are estimated. The characteristic $T_1$ times of the surface-wetting phase can also be used to estimate formation pore size distributions and formation permeability.

In one aspect of this application, stacking of multiple echo train data may be used to reduce the effect of noise and increase the SNR of signals from deep volumes. Such stacking mechanism will require, however, assumption that noise is of random nature. Thus, for example, the average echo train from 10 events is affected with much less noise than the echo train from a single event. (In general, if N is the number of stacked signals, the SNR of the averaged signal improves as $\sqrt{N}$). Various methods exist to perform stacking such as, for example, using two pulse sequences of opposite phase that cancel electronic offsets and 180° ringing, pulse sequences is known as phase-alternated pair (PAP).

In another embodiment, time-domain averaging of the received signal may be used to improve SNR of the deep measurements as disclosed in U.S. patent application Ser. No. 09/803,819, owned by the assignee of the present application and incorporated herein by reference. In particular, such averaging technique involves constructing a time-domain averaged NMR echo train, the averaging being performed over time interval $\Delta$ using the expression $$S_\Delta(t) = \int_t^{t+\Delta} dt' S(t')/\Delta$$

where is the provided measurement signal, and the time-domain averaged data train is constructed at times $t=t_0, t_0+\Delta, t_0+2\Delta, \ldots, t_0+N\Delta$. In addition to improving SNR, time-domain-averaging method improves vertical resolution of the NMR tool.

In yet another embodiment, both pulse stacking and time-domain-averaging techniques may be combined to further improve SNR from deep as well as shallow volume.

The foregoing description of the preferred embodiments has been presented for purposes of illustration and description. It is not intended to be exhaustive or to limit the invention(s) to the precise form disclosed. Many modifications and variations will be apparent to those skilled in the art. The embodiments were chosen and described in order to best explain the underlying innovative principles and certain illustrative practical applications, thereby enabling others skilled in the art to make and use the invention(s). Various embodiments and modifications that are suited to a particular use are contemplated. It is intended that the scope of the invention(s) be defined by the accompanying claims and their equivalents.

What is claimed is:

1. A system for NMR logging of an underground formation traversed by a borehole, the system having a longitudinal axis and comprising:

means for imparting a static magnetic field in the formation surrounding the borehole, the static magnetic field being substantially radially-oriented with respect to the longitudinal axis in a portion of the formation;

means for applying a first oscillating magnetic field having magnetic field lines substantially orthogonal to the static magnetic field in substantially all azimuthal directions;

means for applying one or more directional oscillating magnetic fields being substantially orthogonal to the static magnetic field in corresponding one or more angular sectors of a volume in the formation surrounding the system; and means for directionally sensitive detection of NMR signals from the formation surrounding the system.

2. The system of claim 1, wherein the means for imparting a static magnetic field comprise at least two tubular magnetic configurations having longitudinal polarization and positioned with like poles facing each other.

3. The system of claim 2, wherein each magnetic configuration comprises a permanent magnet, and a plurality of pole pieces longitudinally extending one or more poles thereof.

4. The system of claim 1, wherein the means for imparting a static magnetic field comprises one permanent magnet and a plurality of pole pieces longitudinally extending one or more poles thereof, to simulate a magnetic monopole in a region of the formation surrounding the system.

5. The system of claim 1, wherein the means for applying a first oscillating magnetic field comprise at least one solenoid coil.

6. The system of claim 5, wherein the first and second saddle coils have planes orthogonal to each other.

7. The system of claim 5 further comprising a soft magnetic core longitudinally disposed around the axis.

8. The system of claim 7, wherein the at least one solenoid coil is wound around the core for producing axially-oriented and azimuthally symmetric oscillating magnetic fields in the formation surrounding the borehole.

9. The system of claim 1, wherein the means for applying one or more directional oscillating magnetic fields comprises a first and second saddle coils.

10. The system of claim 9 further comprising a soft magnetic core longitudinally disposed around the axis.

11. The system of claim 10, wherein the first and second saddle coils are disposed substantially orthogonally with respect to each other around the core and capable of receiving azimuthally asymmetric NMR signals from a sensitive region in the formation.

12. The system of claim 1, wherein the means for applying one or more directional oscillating magnetic fields comprises a plurality of antenna segments formed of solenoids, and disposed symmetrically about the longitudinal axis of the tool.

13. The system of claim 12, wherein at least two adjacent antenna segments are separated by a conducting layer to reduce mutual detuning coupling between the at least two adjacent antenna segments.

14. A method for NMR logging a borehole in a geologic formation by means of a tool having longitudinal axis, the method comprising the steps of:
   imparting a static magnetic field having substantially radial orientation with respect to the tool axis in a volume of the formation surrounding the borehole;
   imparting a plurality of oscillating magnetic fields substantially orthogonal to the static magnetic field in the volume of the formation in which the static magnetic field has substantially radial orientation, the plurality of oscillating magnetic fields being azimuthally directional;
   detecting NMR signals from the formation in a plurality of directionally sensitive antenna segments; and
   processing of the detected NMR signals to obtain directionally sensitive information about at least one property of the formation.

15. The method of claim 14, wherein the plurality of directionally sensitive antenna segments detect NMR signals from angular sectors of approximately 90 degrees.

16. A method for determining an NMR property of formation surrounding a borehole with the aid of a logging device, comprising the steps of:
   providing a magnetic configuration producing a substantially radial static magnetic field into a portion of the formation;
   providing a plurality of directionally sensitive antenna segments disposed along a longitudinal axis of the logging device generating RF pulsed magnetic fields in the formation, the RF fields being substantially orthogonal to the static magnetic field;
   receiving NMR signals from a sensitive region of the formation at two adjacent antenna segments; and
   determining a property of the formation in a direction based on orientation of both the adjacent antenna segments.

17. The method of claim 16, wherein the plurality of antenna segments are disposed substantially symmetrically about the longitudinal axis of the logging device.

18. The method of claim 16, wherein at least one of the plurality of antenna segments comprises (i) a soft-magnetic core and (ii) at least one antenna coil located outside the soft-magnetic core.

19. The method of claim 16, wherein at least four antenna segments are disposed along the longitudinal axis of the logging device.

20. The method of claim 16, wherein the direction based on orientation of both the adjacent antenna segments for the property of the formation is approximately intermediate between the orientation of each of the adjacent antenna segments.

21. The method of claim 16, wherein the provided magnet configuration comprises two magnets polarized along a longitudinal axis of the logging device, the magnets having like poles facing each other.

22. The method of claim 16 further comprising the step of energizing fewer than all in the plurality of directionally sensitive antenna segments.

23. The method of claim 22, wherein two adjacent antenna segments are energized to provide RF magnetic fields.

24. The method of claim 16 further comprising the step of providing a plurality of RF pulses at corresponding plurality of frequencies to probe different sensitive regions of the formation.

25. The method of claim 16, wherein the magnetic configuration simulates a magnetic monopole about the plurality of antenna segments.

26. The method of claim 16 further comprising determining a directional property of the formation from signals received in four symmetrically placed antenna segments in accordance with:

$$\begin{bmatrix} N \\ E \\ S \\ W \end{bmatrix} - \begin{bmatrix} 1001 \\ 1100 \\ 0110 \\ 0011 \end{bmatrix} X \begin{bmatrix} NE \\ SE \\ SW \\ NW \end{bmatrix} \to \min, \text{ for } \begin{bmatrix} N \\ E \\ S \\ W \end{bmatrix} \geq 0;$$

wherein N, E, S, and W, respectively stand for a value of the property in each of four symmetrically placed directions and NE, SE, SW, and NW stand for respective quantities related to the signals detected in four symmetric antennas segments facing four intermediate directions with reference to the four symmetric directions.

* * * * *